(12) United States Patent
Moon et al.

(10) Patent No.: US 11,801,228 B2
(45) Date of Patent: *Oct. 31, 2023

(54) MODIFIED GUANIDINE-CONTAINING POLYMERS FOR BIOLOGIC DELIVERY

(71) Applicants: Joong Ho Moon, Weston, FL (US); Alfonso Barrios, Miami, FL (US); Mario Diaz, Miami, FL (US)

(72) Inventors: Joong Ho Moon, Weston, FL (US); Alfonso Barrios, Miami, FL (US); Mario Diaz, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/965,330

(22) Filed: Oct. 13, 2022

(65) Prior Publication Data

US 2023/0225982 A1    Jul. 20, 2023

Related U.S. Application Data

(63) Continuation of application No. 17/578,709, filed on Jan. 19, 2022, now Pat. No. 11,529,315.

(51) Int. Cl.
| | |
|---|---|
| *A61K 47/32* | (2006.01) |
| *A61K 9/51* | (2006.01) |
| *A61K 47/34* | (2017.01) |
| *A61P 43/00* | (2006.01) |
| *C07D 491/048* | (2006.01) |

(Continued)

(52) U.S. Cl.
CPC .......... *A61K 9/5138* (2013.01); *A61K 9/5115* (2013.01); *A61K 47/32* (2013.01); *A61K 47/34* (2013.01); *A61P 43/00* (2018.01); *C07D 491/048* (2013.01); *C08G 61/125* (2013.01); *B82Y 5/00* (2013.01); *C08G 2261/1432* (2013.01); *C08G 2261/3342* (2013.01)

(58) Field of Classification Search
None
See application file for complete search history.

(56) References Cited

U.S. PATENT DOCUMENTS

| | | |
|---|---|---|
| 10,568,902 B2 | 2/2020 | Moon et al. |
| 10,688,189 B1 | 6/2020 | Moon et al. |

OTHER PUBLICATIONS 17578709 structure search Jul. 5, 2022 (Year: 2022).*

(Continued)

*Primary Examiner* — Peter A Salamon
(74) *Attorney, Agent, or Firm* — SALIWANCHIK, LLOYD & EISENSCHENK

(57) ABSTRACT

The subject invention provides materials and methods for intracellular deliver of molecules and/or therapeutic agents. The subject invention also provides methods for synthesizing polymeric systems and nanomaterials that enhance or assist the passage of molecules and/or therapeutic agents across biological membranes. The compound, polymer or nanoparticle of the subject invention comprises a modified guanidine moiety in a plurality of repeating units of a polymer or on the surface of a nanoparticle where the guanidine moiety comprises, for example, a carbamoyl or thiourea modification. The polymer or nanoparticle can be used in a cancer treatment formulation.

12 Claims, 14 Drawing Sheets
(14 of 14 Drawing Sheet(s) Filed in Color)

(51) Int. Cl.
*C08G 61/12* (2006.01)
*B82Y 5/00* (2011.01)

(56) References Cited

OTHER PUBLICATIONS

Herbstein, Frank H. et al. "Bis(phenyl)-1-carbamoylguanidinium N-Phenylcarbamidonitrilate. Revision of an Earlier Proposal", Acta Cryst. C53, pp. 922-925, 1997.
Tilley, Jefferson W. et al., "The Synthesis of 3,5-Diamino-1,2,4-oxadiazoles," Helvetica Chimica ACTA, vol. 63, Fasc. 4 (1980)—No. 90, p. 841-859.

* cited by examiner

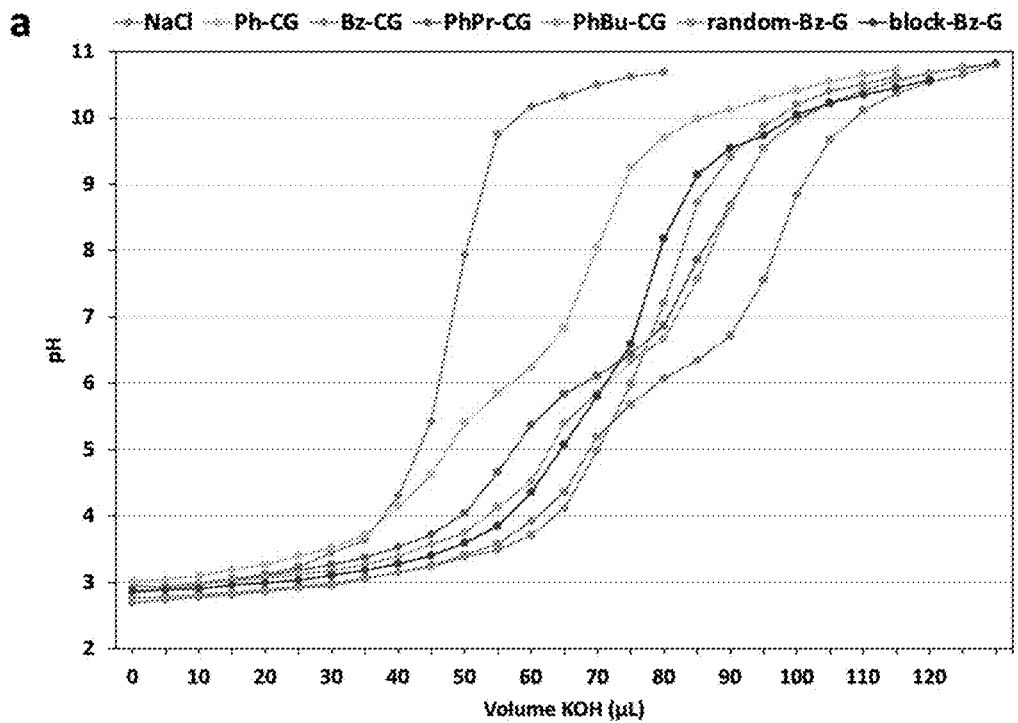
FIG. 3A
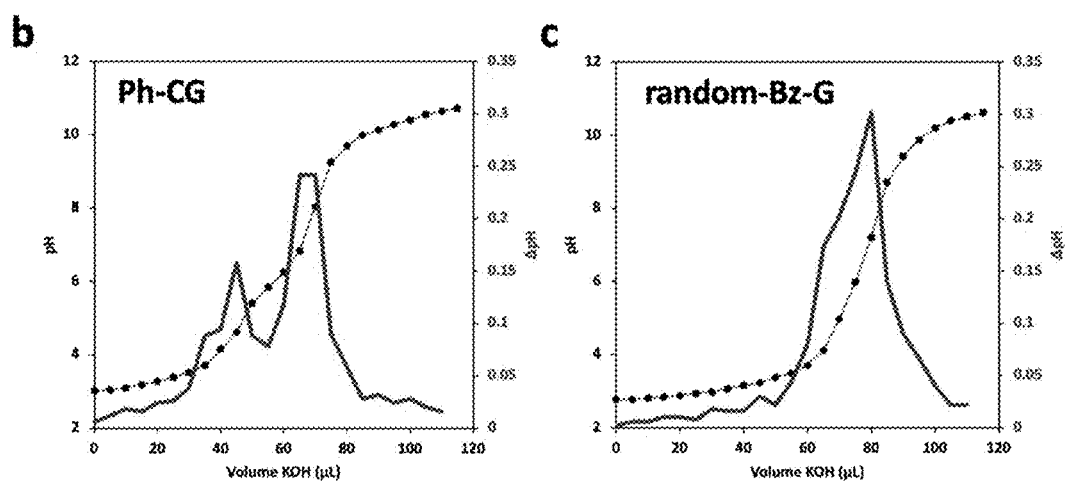
FIG. 3B
FIG. 3C

MODIFIED GUANIDINE-CONTAINING POLYMERS FOR BIOLOGIC DELIVERY

CROSS-REFERENCE TO A RELATED APPLICATION

This application is a continuation application of U.S. Ser. No. 17/578,709, filed Jan. 19, 2022, which is incorporated herein by reference in its entirety.

GOVERNMENT SUPPORT

This invention was made with government support under DMR2105016 awarded by the National Science Foundation. The government has certain rights in the invention.

BACKGROUND OF INVENTION

The design and synthesis of novel nanomaterials that enhance or assist the passage of biologics, such as proteins, enzymes, and antibodies, across cellular membranes is of significant importance. Cell membranes are impermeable to most macromolecules. Many drug candidates fail to advance clinically because they do not have the properties needed to cross biological membranes and reach their intracellular target. Additionally, poor pharmacokinetics, stability, and off-target effects lead to undesirable biological responses.

The cytosolic delivery of functional proteins could lead to an efficient and specific control of cellular processes for various disease treatments. Despite the success and promise of the first protein-based drugs, current protein-based therapeutics are mainly designed to target the extracellular receptors or secretory proteins due to the cell membrane impermeability of most proteins.

Moreover, many standard laboratory techniques, such as immunostaining and gene editing, may require the intracellular accumulation of proteins inside the cell. A major bottleneck in the advancement of biologics development is due to the membrane impermeability of most proteins, and a lack of effective approaches to delivering proteins to intracellular targets. Current commercially available materials face severe limitations for use, prompting the need for improved protein delivery systems.

The covalent modification of proteins with membrane translocating moieties has been used, however, the risk of altered structure and function has led to significant focus on non-covalent methods. Lipids, peptides, and polymers all rely on relatively weak, non-covalent interactions between the carrier and cargo. The synergistic inter-macromolecular ionic, hydrophobic, and hydrogen bond interactions are essential to achieve proper complexation between the carrier and cargo, interaction with the cellular membrane, and release of the protein inside the cell.

Numerous synthetic polymeric carriers have been developed for the transport of proteins across cell membranes. Specifically, guanidine-rich polymers, relying on the key functional group of cell-penetrating peptides, have gained attention. Due to the unique delocalized positive charge of guanidine, strong ionic and hydrophobic interactions exist with the biomacromolecule cargo. Additionally, the capability of bidentate hydrogen bond interactions assists in the assembly of complexes and cellular entry, especially when multiple guanidine units collectively interact with biomacromolecules in a relatively hydrophobic environment.

Despite the significant advantages, the high positive charge density of guanidine-rich carriers, often results in poor complex stability due to non-specific interactions with other macromolecules in physiological relevant environments, resulting in poor outcomes. For example, the same positive charge is often responsible for nonspecific binding with serum proteins, resulting in destabilization of protein/carrier complexes, alteration of cellular entry pathways, and diminishing overall intracellular entry efficiency. The hydrogen bond interactions in aqueous environments are also dramatically weakened as a large excess of water molecules strongly interacts with guanidine. Therefore, guanidine-based protein delivery systems perform poorly in serum-containing media.

Thus, there is a need to develop novel delivery materials, such as guanidine-rich compounds, carriers or polymers with improved efficacy and balanced hydrophobicity, which overcome the biological barrier. There is also a need to develop methods and approaches for modification and synthesis of guanidine derivatives with improved efficacy.

BRIEF SUMMARY

The subject invention provides materials and methods for intracellular delivery of molecules or therapeutic agents such as drugs, nucleic acids, and proteins. In one embodiment, the subject invention provides nanomaterials as molecule transporters or carriers for targeted delivery of therapeutic agents into cells, preferably, cancer cells for inhibiting the growth of cancer cells and altering gene expression in these cells.

In one embodiment, the nanomaterial of the subject invention comprises a polymer or nanoparticle that comprises a modified guanidine moiety in a plurality of repeating units of a polymer, or on the surface of a nanoparticle.

In one embodiment, the modified guanidine moiety comprises a direct conjugation of a planar carbamoyl group to guanidine, which decreases the pKa, leading to a decreased positive charge environment. Additionally, the hydrogen bonding moiety is extended by the carbamoyl group. This reduced positive charge density, together with new hydrogen bond site, can lead to enhanced interactions between the carrier and cargo, and ultimately, improved protein delivery efficacy.

In a specific embodiment, the nanomaterial or polymer of the subject invention is a guanidylcarbamoyl or carbamoylguanidine derivative. Advantageously, the nanomaterials or polymers having such novel functional groups dramatically enhance intracellular biologics delivery efficiency by improving serum stability, intracellular entry, and release of payloads. Thus, the nanomaterials and polymers of the subject invention function well in the absence or presence of serum, which is superior compared to the existing cargo delivery materials.

For example, the coplanar phenyl group connected carbamoylguanidine derivative exhibits efficient delivery of proteins with various sizes and isoelectric points. The carbamoylguanidine derivative successfully delivers apoptosis-inducing proteins even in a serum containing medium, as compared with most protein delivery systems that show a sharp efficiency decrease in the presence of serum.

In one embodiment, the subject invention provides a guanidine modification to substantially improve functional protein delivery efficiency. The decreased pKa of planar carbamoylguanidine increases local hydrophobicity and hydrogen bond interactions, allowing the formation of stable protein complexes with improved complex stability in a serum-containing medium. The coplanarity of the phenyl group directly introduced to carbamoylguanidine plays a significant role in the cellular entry. The developed functional groups can be introduced to many existing biologic delivery platforms to tackle the issues associated with therapeutic protein delivery.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 3A-3C show the pKa determination. (3A) pH titration curves of PNs with KOH from pH 3 to 11. (3B-3C) Method for pKa determination of Ph-CG (3B) and random-Bz-G (3C). No value was determined using this method for random-Bz-G as there is only 1 maximum ΔpH.

DETAILED DISCLOSURE

Figure 1:
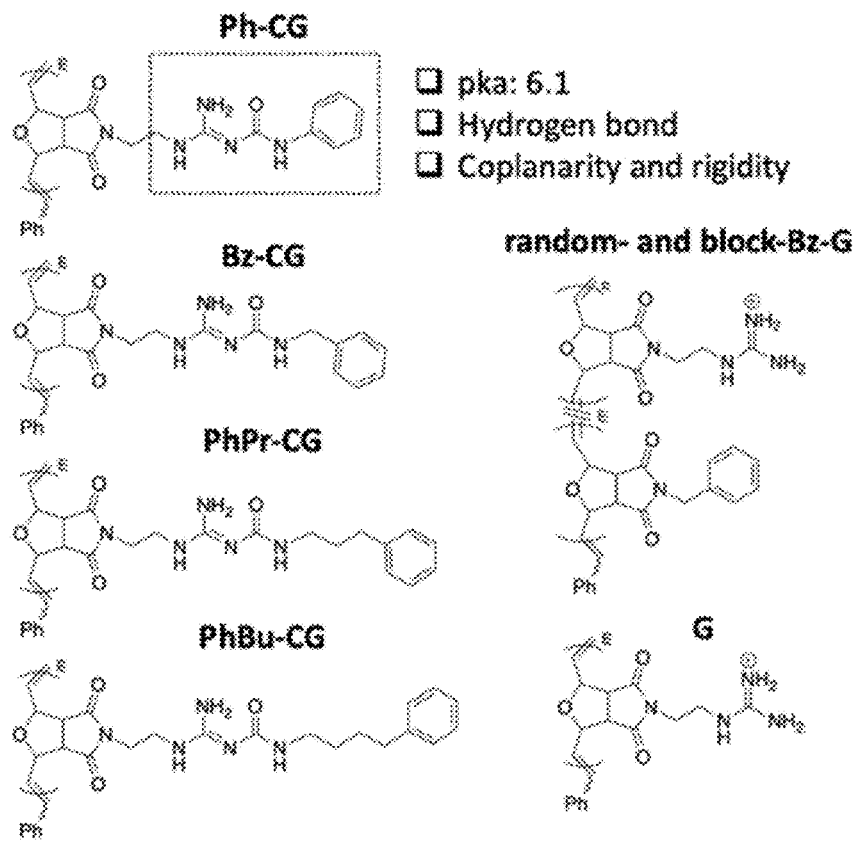
FIG. 1 shows chemical structures of PNs containing various functional groups. CG: Carbamoylated (Cbm) Guanidine (G); Ph: Phenyl; Bz: Benzyl; PhPr: Phenylpropyl; and PhBu: Phenylbutyl.

The subject invention provides materials and methods for intracellular deliver of molecules and/or therapeutic agents such as drugs, nucleic acids, peptides, dyes and proteins. The subject invention also provides methods for the design and synthesis of polymeric systems and nanomaterials that enhance or assist the passage of therapeutic agents across biological membranes.

In one embodiment, the subject invention provides polymeric systems comprising cell-penetrating peptide (CPP)-like moieties for transporting therapeutic agents and/or biological molecules across biological membranes. The polymeric systems can be used as molecular transporters or carriers that facilitate the internalization of therapeutic agents and/or biological molecules by cells. Advantageously, the properties of the polymeric systems can be tuned by modulating the chemistry and architecture of the materials. Specifically, by retaining only the key features of CPPs necessary for sufficient internalization and delivery of the cargo, CPP synthetic mimics (CPPMs) have improved properties compared to naturally occurring CPPs.

In one embodiment, the subject invention provides molecular transporters for intracellularly delivering molecules and/or therapeutic agents such as drugs, nucleic acids, peptides, dyes and proteins. In one embodiment, the molecular transporter comprises a material including, for example, organic/inorganic compounds, synthetic polymers, dendrimers, natural polymers, polysaccharides, proteins, peptides, antibodies, nucleic acids, metal organic framework, metallic nanoparticles, inorganic nanoparticles, and porous nanoparticles.

In one embodiment, the molecular transporters of the subject invention can be synthesized using ring-opening metathesis polymerization (ROMP). ROMP has great benefits over other polymerization techniques, which include controlled polymer length, low polydispersity index (PDI) and easy copolymer design.

In one embodiment, the molecular transporter comprises a compound, polymer or nanoparticle comprising one or more structures/functional groups selected from

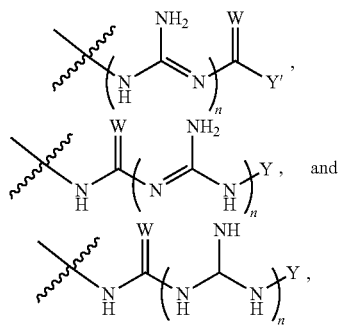

wherein n≥1; W is O, S or Se; and Y and Y' can be any functional group. Preferably, Y and Y' are each independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkoxy, substituted alkoxy, amino, alkynyl, hydroxyl, haloalkyl, acyl, alkylamino, arylamino and hydroxylalkyl.

In a preferred embodiment, Y' is —NHR1, or —NR1R2; and n is 1-10, wherein R1 and R2 are each independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkoxy, substituted alkoxy, alkynyl, hydroxyl, haloalkyl, acyl, alkylamino, arylamino and hydroxylalkyl.

In one embodiment, the molecular transporter comprises a compound, polymer or nanoparticle comprising one or more structures/functional groups selected from

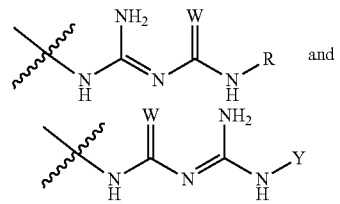

in a plurality of repeating units of the compound or polymer, or on the surface of a nanoparticle, wherein W is O, S, or Se; R and Y each independently can be any functional group. Preferably, R and Y are each independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkoxy, substituted alkoxy, alkynyl, haloalkyl, amino, acyl, alkylamino, acylamino and hydroxylalkyl.

In specific embodiments, the molecular transporter comprises a compound, polymer or nanoparticle comprising a guanidylcarbamoyl or carbamoylguanidine group in a plurality of repeating units of a compound or polymer, or on the surface of a nanoparticle.

In one embodiment, the compound or polymer of the subject invention is a guanidylcarbamoyl derivative (e.g., GuanidinylCarbamoyl Benzene (GCB)) or a carbamoylguanidine derivative (e.g., CarbamoylGuanidinyl Pyrimidine (CGP) and CarbamoylGuanidinyl Benzene (CGB)). In specific embodiments, the guanidylcarbamoyl derivative comprises one or more guanidylcarbamoyl groups. The carbamoylguanidine derivative comprises one or more carbamoylguanidine groups.

In certain embodiments, the polymer or compound of the subject invention comprises a direct conjugation of planar carbamoyl (Cbm) group to guanidine. Advantageously, such conjugation decreases the pKa of guanidine, leading to decreased positive charge density in physiological environments. This reduced charge density is expected to increase the local hydrophobicity, which significantly enhances the efficiency of hydrogen bond interactions in combination with the increased number (i.e., tridentate) of hydrogen bond sites of the carbamoylguanidinyl or guanidinylcarbamoyl group.

In a specific embodiment, the guanidylcarbamoyl group has a structure of

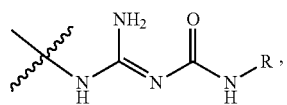

wherein R can be any functional group. Preferably, R is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkoxy, substituted alkoxy, alkynyl, haloalkyl, amino, acyl, alkylamino, arylamino and hydroxylalkyl.

In a specific embodiment, the carbamoylguanidine group has a structure

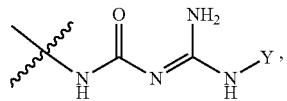

wherein Y can be any functional group. Preferably, Y is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkoxy, substituted alkoxy, alkynyl, amino, haloalkyl, acyl, alkylamino, arylamino and hydroxylalkyl.

In one embodiment, the molecular transporter of the subject invention comprises a conjugated polymer (CP). Biodegradable CPs can be formed by introducing flexible degradable functional groups along the backbone of the CP that can be used for quantitative labeling of mitochondria.

Cellular interaction and internalization of CPs are dependent on the chemical structures of both the backbone and side chains of the CPs. CPs with guanidine units (G-CPs), as disclosed in Moon et al. U.S. Pat. Nos. 9,676,886; 9,757,410; and 10,688,189, which are incorporated herein by reference, enter live cells quickly through the cell membrane.

In specific embodiments, the conjugated polymer comprises poly(phenyleneethynylene), poly(phenylenevinylene), poly(phenylene), poly(fluoreine), polythiophene, or any p-electron conjugated polymers.

In embodiments of the invention, the polymer need not be a conjugated polymer, which is generally ridged, but can be a non-conjugated polymer that has a flexible backbone. In embodiments of the invention, the polymer can have flexible side chains that enhance the water solubility of the polymer. Synthetic and natural polymers that can be employed can be, but are not limited to, amine functionalized polymethacrylates and polyacrylates, branched and linear polyehtyleneimines, polyamidoamine, amine functionalized dendrimers, poly-L-lysine, chitosan, amine functionalized dextran, amine functionalized alginates, amine functionalized heparin, and amine functionalized oligo or polysaccharide.

In embodiments of the invention, nanoparticles are used for efficient intracellular delivery and labeling after modulating surface properties to enhance their initial interaction following entry. The nanoparticles can be those that are metal oxides, metal carbides, metal nitrides, metals, diamond, or any other type of nanoparticle. The polymer can be in the form of a soluble polymer or can be a nanoparticle where the functional groups are of sufficient concentration at the nanoparticle surface to yield a nanoparticle that is decorated with one or more guanidylcarbamoyl and/or carbamoylguanidine groups. The nanoparticles can be of a single structure or a core-shell particle. The particles can inherently have surface functionality that react with guanidylcarbamoyl and/or carbamoylguanidine groups. The particle surface can be functionalized by reaction with an agent, for example, a silane coupling agent, such as, but not limited to, 3-aminopropyltrimethoxy silane, or thiol or disulfide containing alkyls with hydroxyl or amine groups for functionalization of metal nanoparticles.

In one embodiment, the compound/polymer of the subject invention comprises a structure selected from

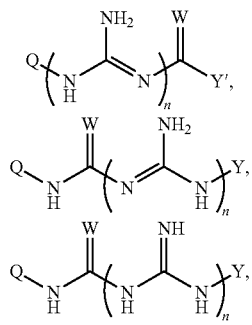

wherein n≥1; W is S, O, or Se; Q, Y and Y' can be any functional group. Preferably, n is 1-10; and Q, Y and Y' are each independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, alkenyl substituted alkenyl, alkynyl, haloalkyl, alkoxy, substituted alkoxy, amino, acyl, alkylamino, arylamino and hydroxylalkyl. More preferably, Y' is —NHR1, or —NR1R2, wherein R1 and R2 are each independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkoxy, substituted alkoxy, alkynyl, hydroxyl, haloalkyl, acyl, alkylamino, arylamino and hydroxylalkyl.

In a preferred embodiment, the functional groups Y, Y' and R show a coplanarity with the Cbm group and/or guanidine. For example, Y, Y' and R may each be independently selected from

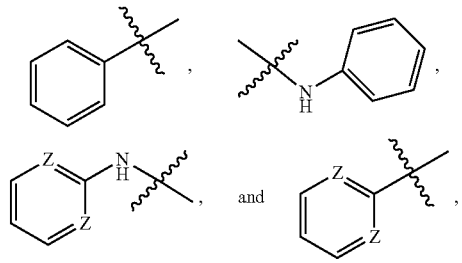

wherein each Z is independently C or N.

In a specific embodiment, the compound/polymer of the subject invention comprises a structure selected from

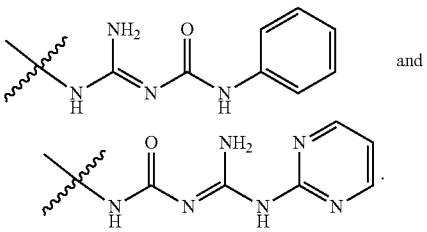

In a specific embodiment, the compound of the subject invention comprises a structure of

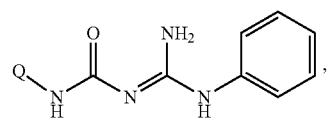

wherein Q can be any functional group. Preferably, Q, is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkoxy, substituted alkoxy, alkynyl, haloalkyl, acyl, alkylamino, arylamino and hydroxylalkyl.

In specific embodiments, the compound of the subject invention has a structure of

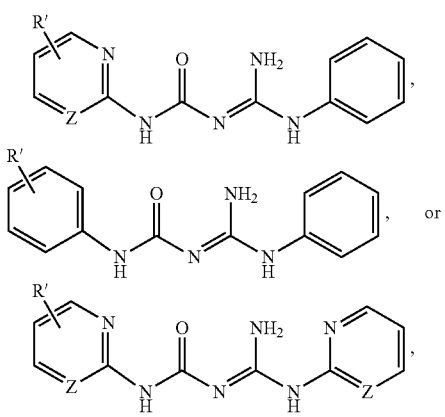

wherein each Z is C or N; and R' can be any functional group. Preferably, R' is selected from, for example, hydrogen, halogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, hydroxyl, alkoxy, substituted alkoxy, alkenyl substituted alkenyl, alkynyl, haloalkyl, amino, acyl, alkylamino, arylamino and hydroxylalkyl.

In one embodiment, the compound/polymer of the subject invention comprises one or more structures/functional groups selected from

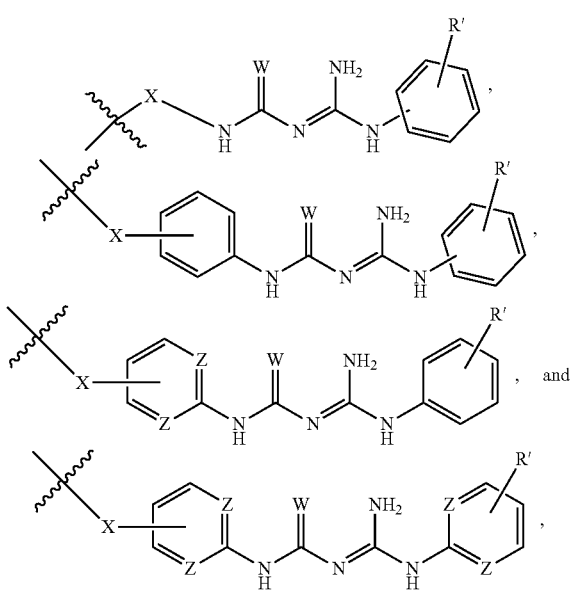

wherein W is S, O, or Se; Z is N or C; X is a linker; and R' is selected from, for example, hydrogen, halogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, amino, hydroxyl, alkoxy, substituted alkoxy, alkynyl, haloalkyl, acyl, alkylamino, arylamino and hydroxylalkyl. In a specific embodiment, the linker may be alkylene, alkoxylene or heteroalkylene, preferably, a short (e.g., C1-C10) alkylene, alkoxylene or heteroalkylene. In a specific embodiment, the linker is ethylene oxide with different lengths, e.g., —(CH$_2$CH$_2$O-)n-, wherein n≥1, preferably, n=1-100.

In one embodiment, the polymeric system/nanocarrier of the subject invention comprises

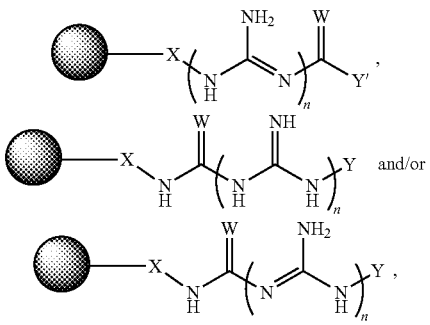

wherein

represents, for example, the backbone of a compound or polymer, polysaccharide, protein, peptide, antibody, nucleic acid, metal organic framework or a nanoparticle; n≥1; W is S, O or Se; X, Y and Y' can be any functional group. Preferably, n is 1-10; X is a linker; and Y and Y' are each independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, alkoxy, substituted alkoxy, hydroxyl, haloalkyl, amino, acyl, alkylamino, arylamino and hydroxylalkyl. More preferably, Y' is —NHR1, or —NR1R2, wherein R1 and R2 are each independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkoxy, substituted alkoxy, alkynyl, hydroxyl, haloalkyl, acyl, alkylamino, arylamino and hydroxylalkyl.

In a specific embodiment, the linker may be alkylene, alkoxylene or heteroalkylene, preferably, a short (e.g., C1-C10) alkylene, alkoxylene or heteroalkylene. In a specific embodiment, the linker is ethylene oxide with different lengths, e.g., —(CH$_2$CH$_2$O-)n-, wherein n≥1, preferably, n=1-100.

In certain embodiments, the compound/polymer/nanoparticle of the subject invention comprises

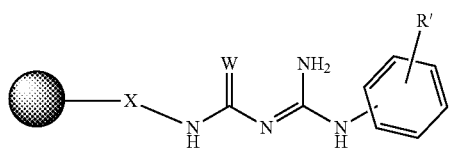

-continued

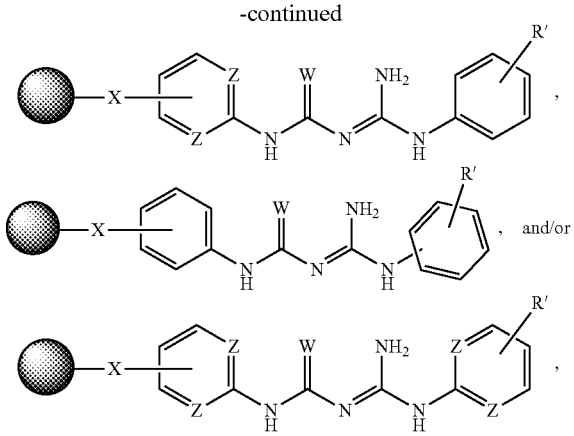

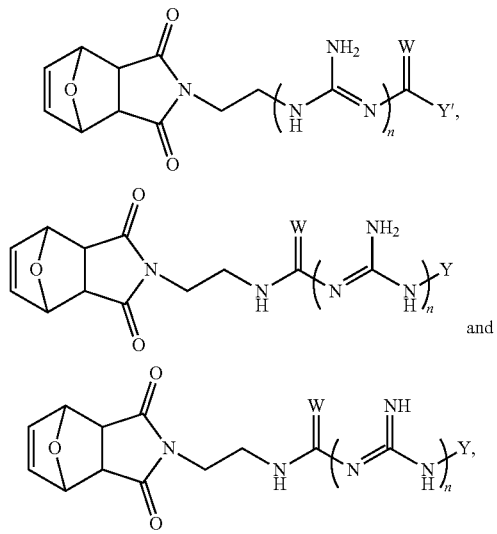

wherein

represents, for example, the backbone of a compound or polymer, polysaccharide, protein, peptide, antibody, nucleic acid, metal organic framework or a nanoparticle; Z is C or N; X is a linker; and R' can be any functional group. Preferably, R' is selected from, for example, hydrogen, halogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, alkoxy, substituted alkoxy, amino, haloalkyl, hydroxyl, acyl, alkylamino, arylamino and hydroxylalkyl.

In a specific embodiment, the linker may be alkylene, alkoxylene or heteroalkylene, preferrably, a short (e.g., C1-C10) alkylene, alkoxylene or heteroalkylene. In a specific embodiment, the linker is ethylene oxide with different lengths, e.g., —(CH$_2$CH$_2$O-)n-, wherein n≥1, preferrably, n=1-100.

In certain embodiments, Y and Y' are each independently carbon or other atoms that result in a pKa higher than 7, the functional group of Y and Y' may be protonated.

In one embodiment, the polymeric system according to the subject invention comprises a compound or polymer comprising one or more guanidylcarbamoyl and/or carbamoylguanidine groups on a plurality of repeating units of the compound or polymer. Advantageously, the direct conjugation of planar carbamoyl group to guanidine in the compounds and polymers of the subject invention decrease the pKa, leading to a decreased positive charge environment. Additionally, the hydrogen bonding moiety is extended by the carbamoyl group. This reduced positive charge density, together with new hydrogen bond site, leads to enhanced interactions between the carrier and cargo, and ultimately, improved protein delivery efficacy.

In one embodiment, the compound/polymer/nanomaterial of the subject invention comprises one or more polynorbornenes (PNs) in the polymeric system.

In one embodiment, the polymer of the subject invention comprises a polymer chain that comprises one or more types of constituent units or repeating units. Preferably, the repeating unit or monomer comprises a structure selected from wherein W is O, S or Se; n≥1; and Y and Y' are each independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkoxy, substituted alkoxy, hydroxyl, alkynyl, haloalkyl, acyl, amino, alkylamino, arylamino and hydroxylalkyl.

In a preferred embodiment, Y' is —NHR1, or —NR1R2, wherein R1 and R2 are each independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkoxy, substituted alkoxy, alkynyl, hydroxyl, haloalkyl, acyl, alkylamino, arylamino and hydroxylalkyl.

In some embodiments, Y and Y' are each independently selected from N-alkylamino; N-arylamino; N-(alkylaryl)amino; N-(aryalkyl)amino; N, N-dialkylamin; N, N-diarylamino; N, N-di(alkylaryl)amino; N, N-di(aryalkylamino); N-alkyl, N-arylamino; N-alkyl, N-(alkylaryl)amino; N-alkyl, N-(arylalkyl)amino; N-aryl, N-(alkylaryl)amino; N-aryl, N-(arylalkyl)amino; unsubstituted or substituted morpholine; unsubstituted or substituted pyrolidine; unsubstituted or substituted pyrrole; unsubstituted or substituted piperidine; unsubstituted or substituted ethyleneimine; unsubstituted or substituted indole; unsubstituted or substituted isoindole; unsubstituted or substituted carbazole; imidazole or substituted imidazole; purine or substituted purine; aminoethanol; amino terminal polyethylene oxide, substituted or unsubstituted alky carbamate, substituted or unsubstituted aryl carbamate, substituted or unsubstituted alkylaryl carbamate and substituted or unsubstituted aryalkyl carbamate. In a specific embodiment, Y and Y' are each independently selected from phenyl (Ph), benzyl (Bz), phenylpropyl (PhPr), phenylbutyl (PhBu), hexylamine (HA), benzylamine (BA), and aminoethoxyethanol (AEE).

In specific embodiments, the monomer comprises or has a structure selected from:

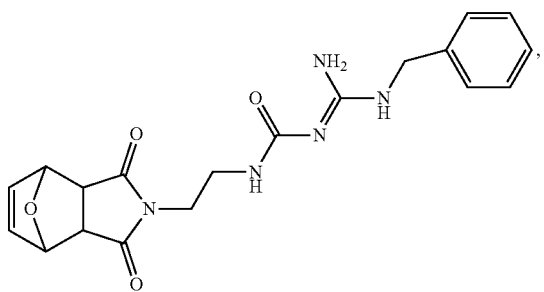

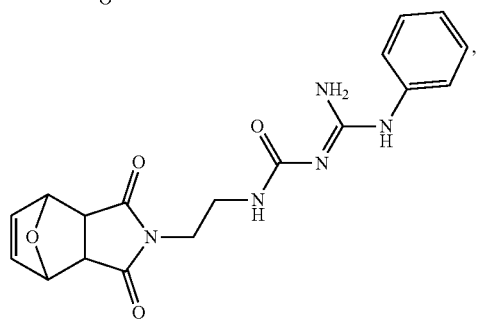

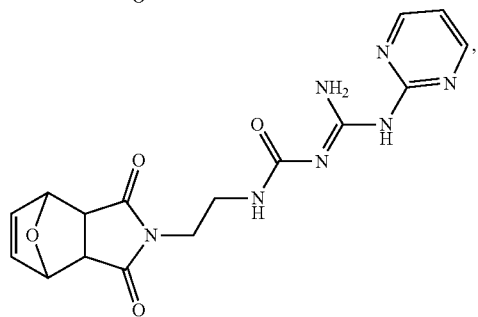

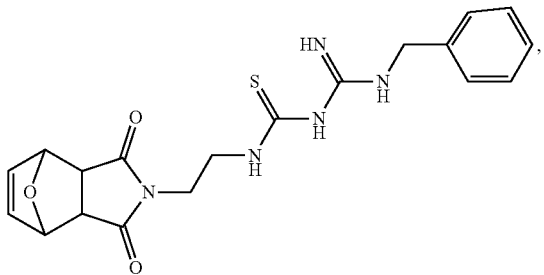

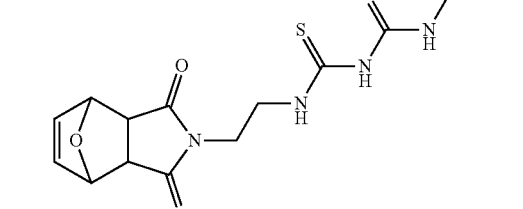

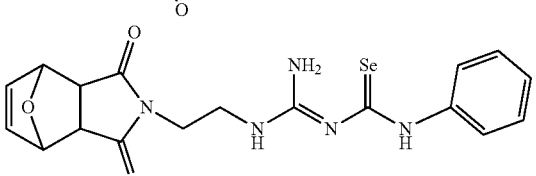
and

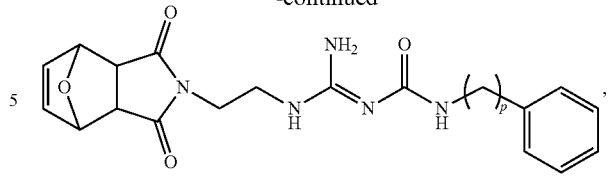

wherein p≥0.

In a specific embodiment, the monomer comprises or has a structure of

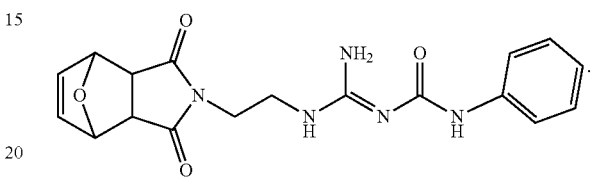

In one embodiment, the polymer is a homopolymer that comprises a structure selected from

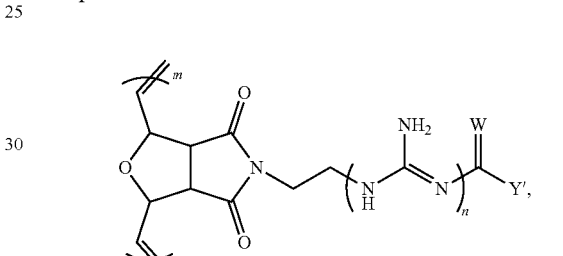

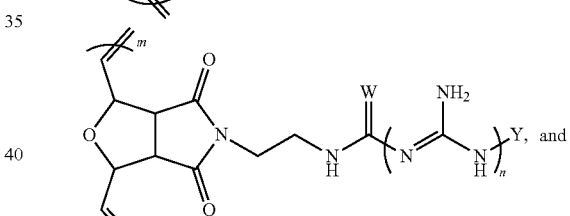

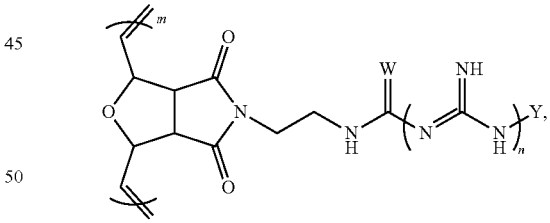

wherein m≥2; n≥1; W is S, O or Se; and Y and Y' are each independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, and substituted cycloalkenyl, alkenyl and substituted alkenyl, alkynyl, alkoxy, substituted alkoxy, hydroxyl, haloalkyl, acyl, amino, alkylamino, arylamino and hydroxylalkyl.

In one embodiment, n is 2-100, 2-90, 2-80, 2-70, 2-60, 2-50, 2-40, 2-30, 2-20, or 2-10. In one embodiment, p is 0-20. Preferably, p is 0-10. More preferably, p is 0-5.

In one embodiment, the polymer is a homopolymer that comprises a structure selected from:

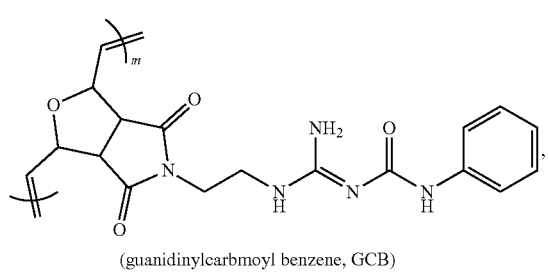
(guanidinylcarbmoyl benzene, GCB)
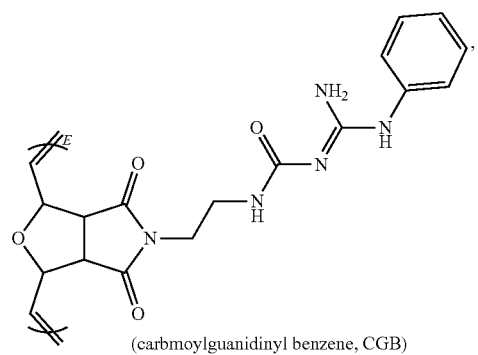
(carbmoylguanidinyl benzene, CGB)
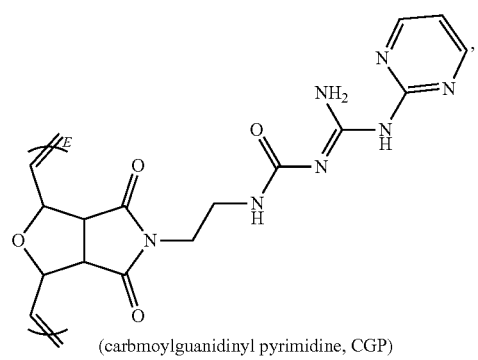
(carbmoylguanidinyl pyrimidine, CGP)
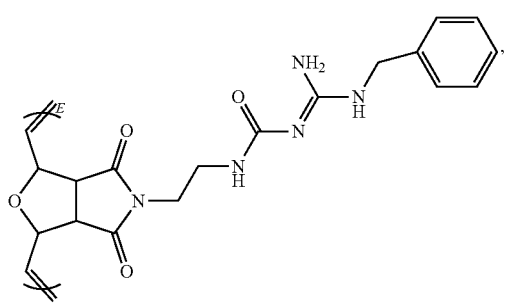
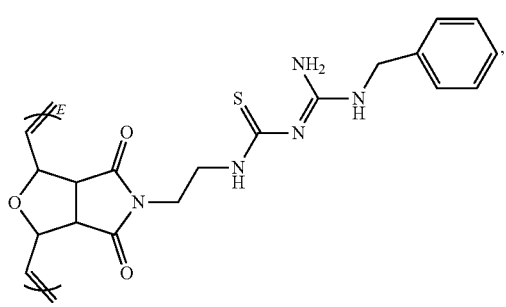
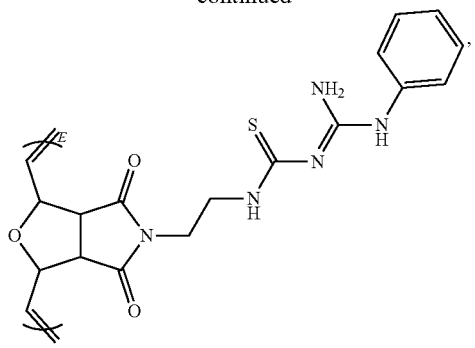
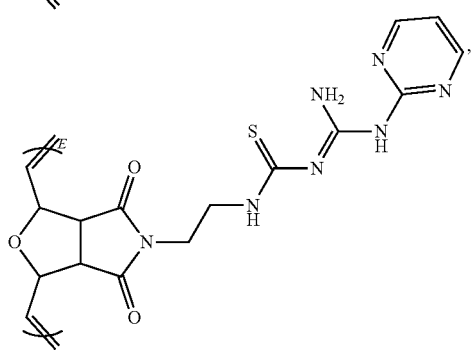
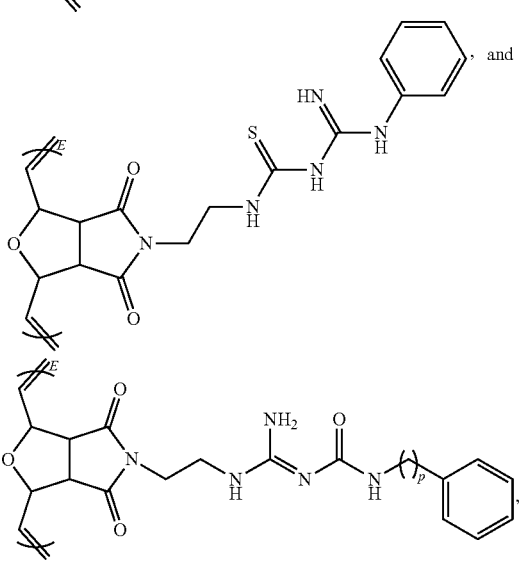
, and
wherein p≥0; and m≥2.
In a specific embodiment, the polymer is a homopolymer that comprises the structure of
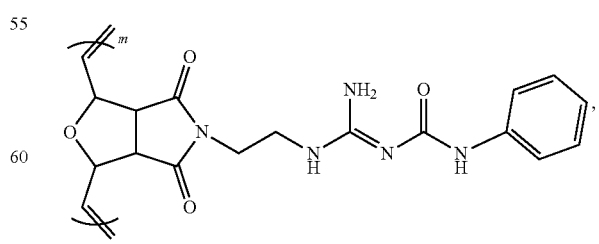
Ph-CG
wherein m≥2.

In some embodiments, the polymer of the subject invention further comprises a functional group (e.g., phenyl) at the end of the polymer chain. Such polymer may have a structure of, for example,

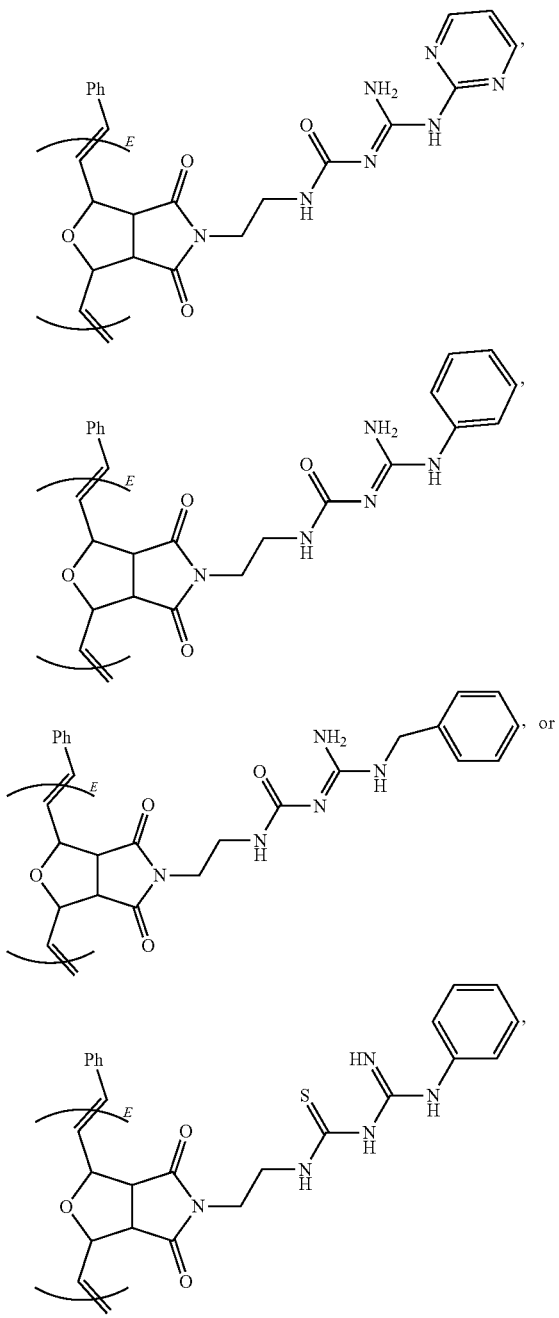

wherein m≥2.

In one embodiment, the polymer is a copolymer comprises a polymer chain that comprises two or more types of constituent units or repeating units. In a further embodiment, the copolymer may be a bipolymer that is obtained by copolymerization of two monomer species, a terpolymer that is obtained by copolymerization of three monomer species, or a quaterpolymer that is obtained by copolymerization of four monomer species.

In one embodiment, the polymer of the subject invention further comprises one or more repeating units or monomer species selected from

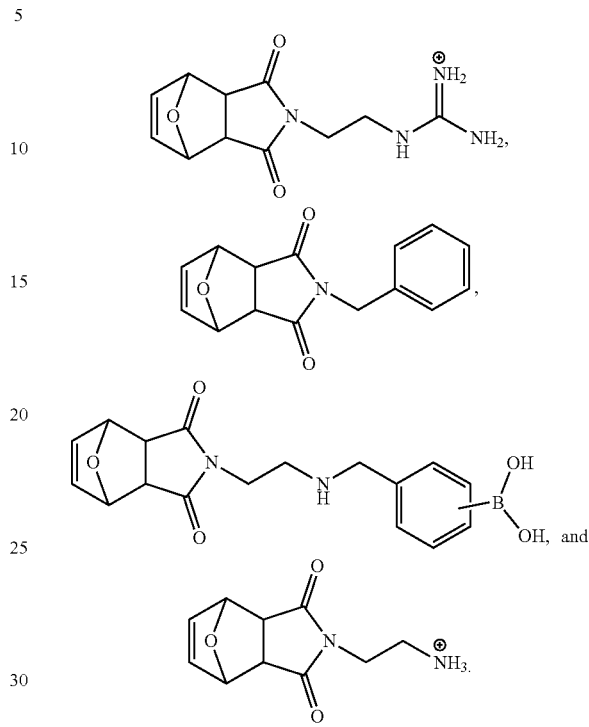

In one embodiment, the copolymer is an alternating copolymer, periodic copolymer, random copolymer or block copolymer. An alternating copolymer is a copolymer comprising two species of monomeric units distributed in alternating sequence, for example, -ABABABAB- or -(AB)n-. A random copolymer is a copolymer comprising two or more types of monomer species with each monomer residue located randomly in the polymer molecule, for example, -AAAABBBABBA-, or -AAAABCBBCBACCBC-. A periodic copolymer a copolymer comprising two or more types of monomer species and has units arranged in a repeating sequence, for example, -(ABABBAAAABBB)n-, or -(AABCBAABBBCCAB)n-. A block copolymer is a copolymer comprising two or more blocks of different homopolymers chemically attached to each other, e.g., by covalent bonds. For example, a block copolymer having repeating units A and B may be arranged as -AAAAABBBBB- or -AAAAABBBBBAAAAA-.

In one embodiment, the polymer is a block copolymer that induces nanostructure formation, e.g., when in aqueous environment, forming a micelle type nanostructure. Advantageously, the polymers may be used to encapsulate drugs/small molecules. Additionally, these copolymers may be used to complex macromolecules such as proteins where the block structure may enhance the nanoparticle formation.

In one embodiment, the polymer is a block copolymer comprising a polymer chain that comprises one or more blocks of the homopolymer of the subject invention, and the polymer chain further comprises one or more blocks of homopolymer comprising monomer species selected from

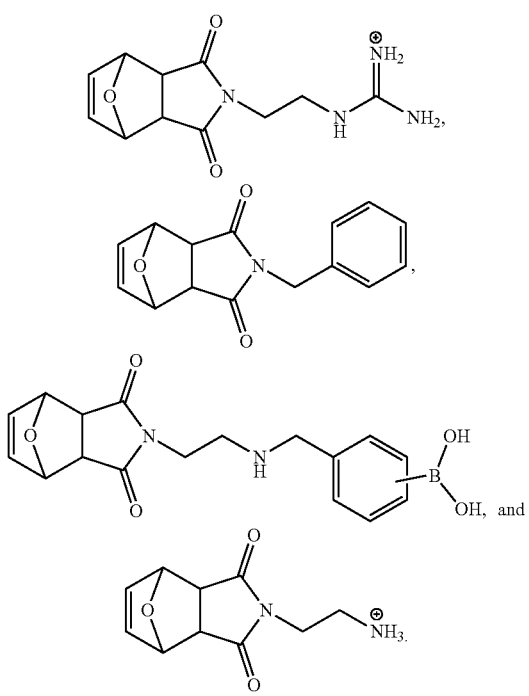

In one embodiment, the homopolymer and/or copolymer of the subject invention comprises one or more boronic acid moieties. Boronic acids have strong binding affinity to biomolecules containing vicinal diols, such as sialic acid. Specifically, boronic acids can target low abundance biomolecules in glucose rich environments. Increased levels of sialic acid have been observed in many cancer cell lines. Thus, such copolymer containing boronic acid moieties may be used as a targeted therapy for cancer treatments. Specifically, ligand affinity and specificity can be tuned by functionalizing boronic acid probes. Functionalization of phenylboronic acid derivatives changes the pKa of the boronic acid probes and the stability of tumor tissue in the acidic microenvironment.

In one embodiment, the subject invention provides a nanomaterial that comprises a polymer of the subject invention conjugated to the surface of a nanoparticle. The nanoparticle comprises one or more materials selected from silica, alumina, titania, zinc oxide, tin oxide, silver oxide, cuprous oxide, cupric oxide, ceria, vanadium oxide zirconia, molybdenum, tungsten oxide, barium oxide, calcium oxide, iron oxide, and nickel oxide.

In one embodiment, the subject invention also provides a therapeutic formulation comprising the polymer or nanoparticle of the subject invention and a pharmaceutically acceptable carrier, wherein the therapeutic formulation further comprises one or more therapeutic agents, wherein one or more therapeutic agents are encapsulated by, or otherwise associated with, the compound/polymer/nanomaterials of the subject invention.

In one embodiment, the therapeutic formulation of the subject invention comprises a mixture/complex of the polymer or nanoparticle of the subject invention and one or more therapeutic agents, wherein the polymer or nanoparticle is mixed with the therapeutic agent at a concentration ratio ranging, for example, from about 1:1 to about 1000:1, from about 1:1 to about 900:1, from about 1:1 to about 800:1, from about 1:1 to about 700:1, from about 1:1 to about 600:1, from about 1:1 to about 500:1, from about 1:1 to about 400:1, from about 1:1 to about 300:1, from about 1:1 to about 200:1, from about 1:1 to about 100:1, from about 1:1 to about 90:1, from about 1:1 to about 80:1, from about 1:1 to about 70:1, from about 1:1 to about 60:1, from about 1:1 to about 50:1, from about 1:1 to about 40:1, from about 1:1 to about 30:1, from about 1:1 to about 20:1, or from about 1:1 to about 10:1.

"Pharmaceutically acceptable carrier" refers to a diluent, adjuvant, or excipient with which the one or more active agents disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant, or excipient to facilitate administration of the composition disclosed herein and that is compatible therewith. Examples of carriers suitable for use in the pharmaceutical compositions are known in the art and such embodiments are within the purview of the invention. The pharmaceutically acceptable carriers and excipients include, but are not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

In one embodiment, the subject invention further provides methods for treating a cancer, the method comprising administering, to a subject in need of such treatment, an effective amount of the therapeutic formulation of the subject invention.

The term "subject" or "patient," as used herein, describes an organism, including mammals such as primates. Mammalian species that can benefit from the disclosed methods of treatment include, but are not limited to, apes, chimpanzees, orangutans, humans, and monkeys; domesticated animals such as dogs, and cats; live stocks such as horses, cattle, pigs, sheep, goats, and chickens; and other animals such as mice, rats, guinea pigs, and hamsters.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, a symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

In one embodiment, the subject invention provides methods for targeted delivery of a compound or molecule, including therapeutic agents (e.g., drugs, antibodies, DNAs, RNAs such as siRNAs and miRNAs, peptides, and proteins), into cells, preferably cancer cells and epithelium cells, the method comprising contacting the cells with the polymeric system or therapeutic formulation of the subject invention.

In one embodiment, the subject invention provides methods for targeted delivery of a therapeutic agent into cells, preferably cancer cells and epithelium cells, the method comprising contacting the cells with the polymer of the subject invention and the therapeutic agent.

In one embodiment, the subject invention provides methods for targeted delivery of a compound or molecule, including therapeutic agents (e.g., drugs, antibodies, DNAs, RNAs such as siRNAs and miRNAs, peptides, and proteins), into the nuclei of cells, preferably cancer cells and epithelium cells, the method comprising contacting the cells with the polymeric system or therapeutic formulation of the subject invention.

In one embodiment, the subject invention provides methods for targeted delivery of a therapeutic agent into the nuclei of cells, preferably cancer cells and epithelium cells, the method comprising contacting the cells with the polymer of the subject invention and the therapeutic agent.

In one embodiment, the subject invention provides methods for transporting a compound or molecule, including therapeutic agents (e.g., drugs, antibodies, DNAs, RNAs such as siRNAs and miRNAs, peptides, and proteins), across a biological membrane, the method comprising contacting the biological membrane with the polymeric system or formulation of the subject invention. The biological membrane may be, for example, cell membranes, organelle membranes, mucous membranes, basement membranes, and serous membranes.

In one embodiment, the subject invention provides methods for transporting a therapeutic agent across a biological membrane, the method comprising contacting the biological membrane with the polymer of the subject invention and the therapeutic agent.

In one embodiment, the subject invention further provides methods for altering/modulating gene expression in a cell, preferably a cancer cell or an epithelium cell, the method comprising contacting the cell with the polymeric system or therapeutic formulation of the subject invention. Altering/modulating gene expression in a cell includes inhibiting or promoting gene expression in the cell.

In one embodiment, the subject invention further provides methods for altering/modulating gene expression in a cell, preferably a cancer cell or an epithelium cell, the method comprising contacting the cell with the polymer of the subject invention and the therapeutic agent.

In one embodiment, the subject invention further provides methods for inhibiting gene expression in a cell, preferably a cancer cell or an epithelium cell, the method comprising contacting the cell with the polymeric system or therapeutic formulation of the subject invention.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

EXAMPLES

Methods and Materials

Materials

Reagents and solvents were purchased from Fisher Scientific and used without further purification. Deuterated solvents were purchased from Cambridge Isotope Laboratories. The number average molecular weight (Mn), weight average molecular weight (Mw), and polydispersity index (PDI=Mw/Mn) of Polymers were determined by gel permeation chromatography (GPC) against polystyrene standards using a Shimadzu high performance liquid chromatography (HPLC) system fitted with PLgel 5 MIXED-D columns and SPD-20A ultraviolet-visible (UV-vis) detector at a flow rate of 1.0 mL/min. Samples for GPC, small amount of dry polymer was dissolved with 1 mL of HPLC grade THF and then filtered through a 0.45 um polytetrafluoroethylene (PTFE) syringe filter prior injection. UV-vis spectra were recorded using a Varian Cary 50 Bio spectrophotometer. Nuclear magnetic resonance (NMR) spectra were recorded on a 400 MHz Avance Bruker NMR spectrometer. Hydrodynamic diameters were obtained using a LM10 HS (NanoSight, Amesbury, United Kingdom), equipped with a sCMOS camera, a sample chamber with Viton fluoroelastomer O-ring, and a 488 nm blue laser. Zeta potentials were determined by using a Zetasizer Nano-Zs (Zen 3600, Malvern Instruments) using a Zeta dip cell. Fluorescence emission spectra were recorded using a FluoroLog-3 Spectrofluorometer (Horiba). Absorbance measurements were recorded on a Tecan Infinite M1000 Pro microplate well reader at 570 nm. Flow cytometry experiments were done using a BD FACSCelesta system and data was analyzed using FlowJo VX. Confocal laser scanning microscopy images were collected using a Nikon A1R microscope with a 60× objective with oil immersion. DAPI, FITC, and TRITC channels were used for fluorescence detection.

General Methodology of Ring Opening Polymerization (ROMP) Monomer Synthesis:

Described is the synthesis of 3 new monomers containing N-Boc-N-(R)-Guanidyl Carbamoyl derivates that were obtained in three steps (Scheme 1). First, Ethylenediamine is monoprotected using $Boc_2O$ chemistry. Second, Diels Alder adduct (exo-7-oxabicyclo[2.2.1]hept-5-ene-2,3-dicarboxylic anhydride) reacts with the N-Boc-ethylenediamine and then, deprotected with trifluoroacetic acid in methylene chloride. N,N-di-Boc-Guanidines derivates are obtained using N,N'-Di-Boc-pyrazole-1-carboxamidine or 1,3-Bis(tert-butoxycarbonyl)-2-methyl-2-thiopseudourea with Mercury (II) Chloride. The last step is the reaction of the N,N-di-Boc-guanylate subtract with the corresponding unprotected amine obtained on the Diels-Alder adduct obtaining the ROMP's monomers.

Synthesis of Benzyl-N,N-di-Boc-Guanidine 1

N, N'-Di-Boc-pyrazole-1-carboxamidine (11 mmol, 3.4 g) was added to a round bottom flask and dissolved in methylene chloride. Triethylamine (9.3 mmol, 1.3 mL) and Benzylamine (9.3 mmol, 1.02 mL) were added to the flask and the reaction mixture was stirred for 16 hours at room temperature. The crude was diluted to 80 ml of methylene chloride and washed with $H_2O$ (2×100 mL), brine (1×100 mL), dried ($MgSO_4$ anhydrous) and filtered. The solvent was removed in vacuo and the crude was purified by recrystallization using methylene chloride: MeOH, yielding 2.0 g (63%) of compound 1 (Scheme 2).

Scheme 2. Synthesis of Benzyl-N,N-di-Boc-Guanidine.

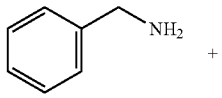

+

Scheme 1. General scheme for the synthesis of ROMP's monomers.

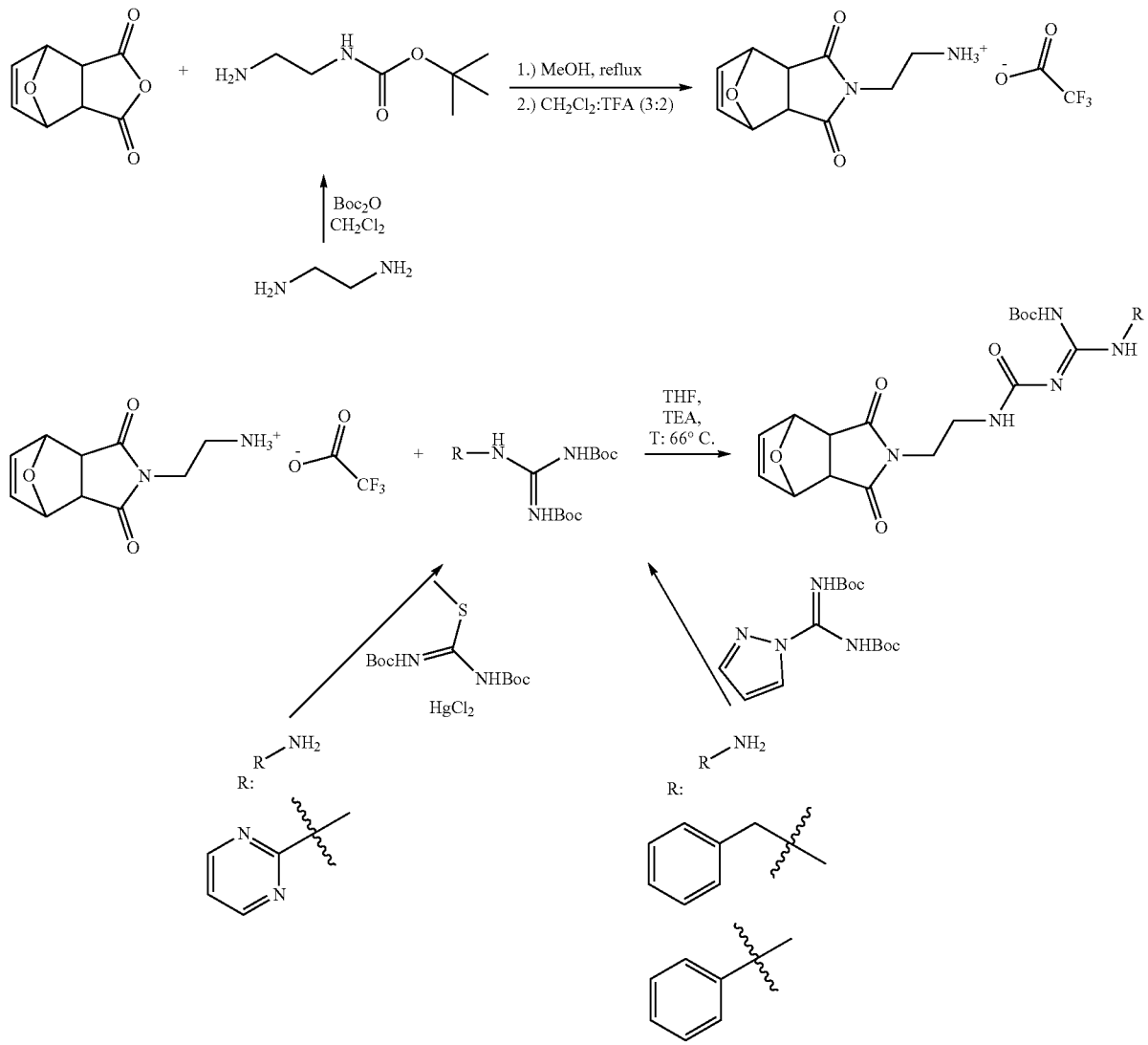

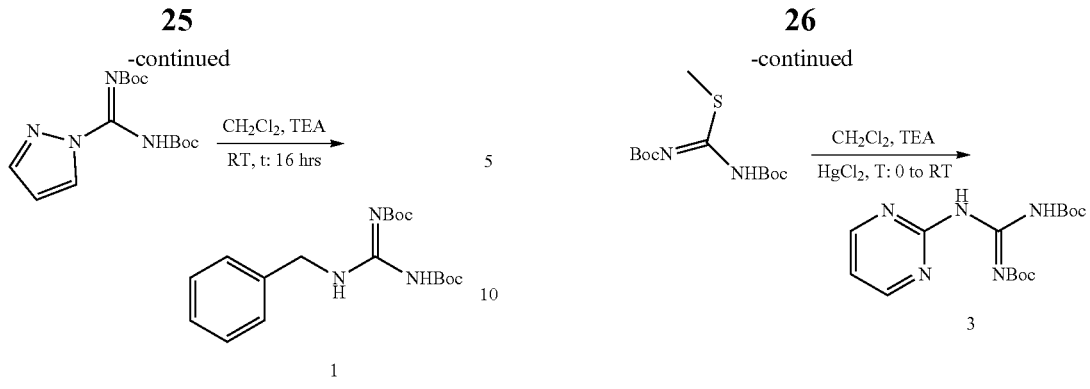

Synthesis of Phenyl-Boc-Guanidine 2

Compound 2 was obtained following the same procedure described below, except for the heating of the reaction mixture at 50° C. The compound 2 was purified by recrystallization in hot MeOH obtaining 892 mg (83%) (Scheme 3).

Scheme 3. Synthesis of Phenyl-Boc-Guanidine.

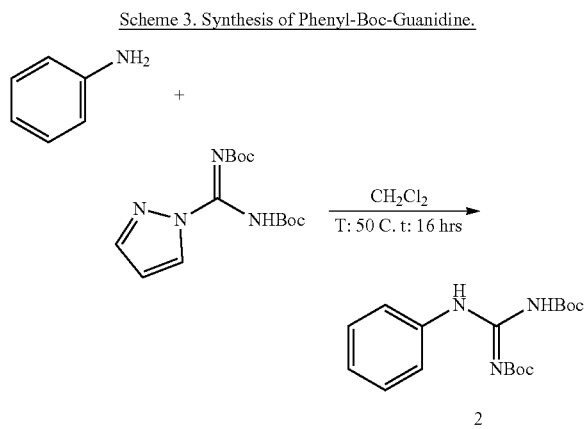

Synthesis of 2-Pyrimidyl-Boc-Guanidine 3

1,3-Bis(tert-butoxycarbonyl)-2-methyl-2-thiopseudourea (5.5 mmol, 1.6 g) and 2-amino-pyrimidine (8.3 mmol, 786 mg) were added to a round bottom flask and dissolved in methylene chloride. Then, Triethylamine (10.5 mmol, 2.3 mL) was added to the stirring solution. The reaction was placed in an ice bath and stirred for 25 minutes (until reach 0° C.). Then, Mercury (II) Chloride (6.06 mmol, 1.65 g) was added, and the reaction was stirred for 48 hrs. The crude was filter through celite pad and washed with H$_2$O (2×5 ml), brine (1×5 ml), dried (MgSO$_4$ anhydrous) and filtered. The crude was purified by column using n-hexane; ethyl acetate (7:3), yielding 1.3 g (70%) of compound 3 (Scheme 4).

Scheme 4. Synthesis of 2-Pyrimidyl-Boc-Guanidine.

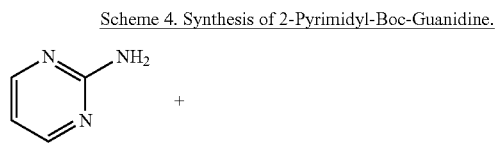

Synthesis of N-Boc-ethylenediamine 4

Ethylenediamine (1.0 mol, 66.6 mL) was added to a round bottom flask containing 800 mL of methylene chloride (Scheme 5). Di-ter-butyl dicarbonate anhydrous (0.15 mol, 32.7 g) were pre-mixed in 300 mL of methylene chloride and added dropwise to ethylenediamine solution. The reaction was stirred for 16 hours, then, the organic phase was washed with H$_2$O (2×800 mL), brine (1×800 mL), dried (MgSO$_4$ anhydrous) and filtered. The solvent was removed in vacuo and a very light-yellow viscous liquid was obtained (78% yield) (Scheme 5).

Scheme 5. Synthesis of N-Boc-Ethylenediamine

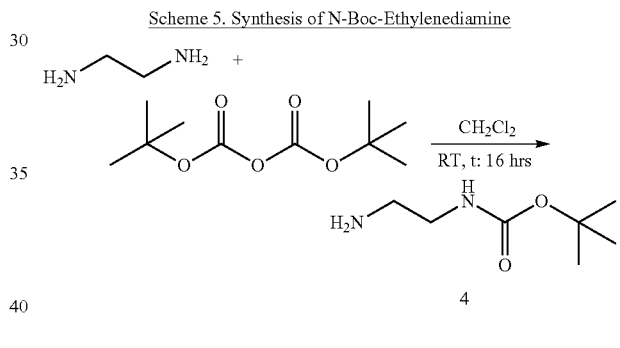

Synthesis of Compound 5

N-Boc-ethylenediamine (39.2 mmol, 6.35 g) and exo-7-oxabicyclo[2.2.1]hept-5-ene-2,3-dicarboxylic anhydride (30.1 mmol, 5 g) was added to a round bottom flask and dissolved in MeOH. Then, Triethylamine (72 mmol, 10 mL) was added, and the reaction mixture was stirred at reflux for 20 hours. Compound 5 precipitated at room temperature and was purified by extraction on methylene chloride and recrystallization using methylene chloride MeOH mixture. The solid obtained (62%) was deprotected using methylene chloride:trifluoracetic acid mixture (3:2). The solvent was removed in vacuo and the crude was purified by precipitation in ether solution yielding pure compound 5 (59%) (Scheme 6).

Scheme 6. Synthesis of Compound 5.

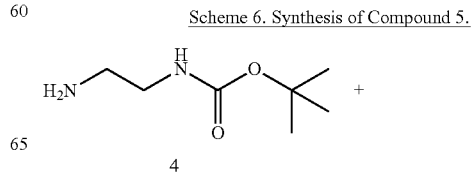

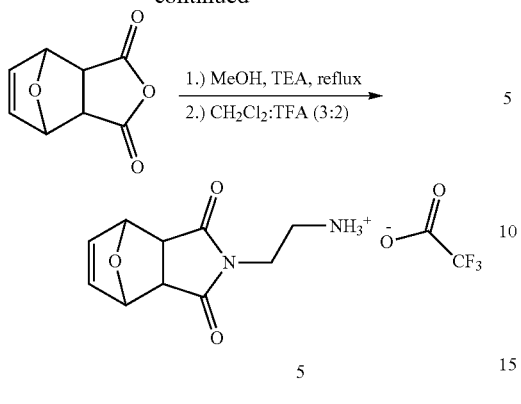

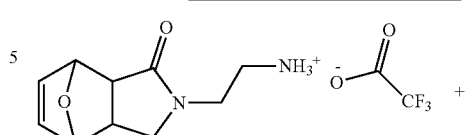

Synthesis of ROMP's monomers 6

Compound 5 (1.24 mmol, 400 mg) and benzyl-N, N-di-Boc-Guanidine (0.992 mmol, 346.6 mg) were added to a round bottom flask and dissolved in THF and Triethylamine (7.44 mmol, 1 mL). The mixture was stirred at reflux for 16 hours. Then, the solvent was removed in vacuo and the crude was diluted in methylene chloride and washed with $NH_4Cl$ (1×10 mL), brine (1×10 mL), dried ($MgSO_4$ anhydrous) and concentrated in vacuo. The crude was purified by flash column using n-Hexane:Ethyl Acetate (2×4:1) and (1×1:1) yielding monomer 6 (45%) (Scheme 7).

Scheme 7. Synthesis of Monomer 6

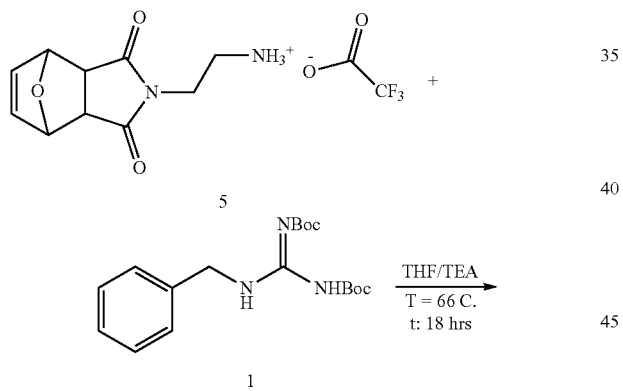

Synthesis of ROMP's Monomer 7

The compound 7 (Scheme 8) was synthesized using the same procedure described below for compound 6. The crude was purified by flash column using n-Hexane:Ethyl Acetate (9:1) and then (4:1), yielding monomer 7 (52%).

Scheme 8. Synthesis of Monomer 7.

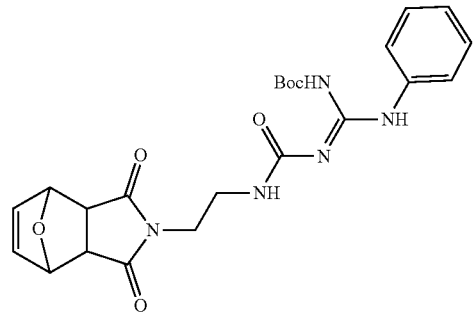

Synthesis of ROMP's Monomer 8

The compound 8 (Scheme 9) was synthesized using the same procedure described below for compound 6. The crude was purified by flash column using Methylene Chloride: Ethyl Acetate (9:1), then (4:1), and finally (7:3), yielding monomer 7 (58%).

Scheme 9. Synthesis of Monomer 8.

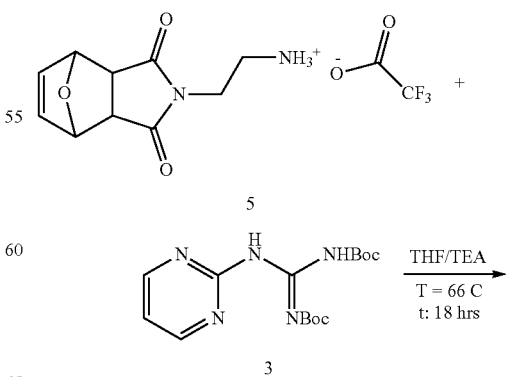

Synthesis of Monomers 13 and 14

Monomers 13 and 14 (Scheme 10) were used for polymerization and synthesized. Briefly, synthesis of monomer 13 began with the N-Boc protection of ethylenediamine with the addition of 0.1 equivalents of di-tert-butyl decarbonate dropwise overnight. N-Boc protected ethylenediamine was refluxed with Diels Alder adduct (exo-7-oxabicyclo[2.2.1]hept-5-ene-2,3-dicarboxylic anhydride) and was precipitated after reaction was complete, yielding compound 12. This compound was deprotected using TFA (to arrive at compound 5) and the free amine was converted to Boc-protected guanidine (to arrive at compound 13). Compound 14 was synthesized by refluxing Diels Alder adduct (exo-7-oxabicyclo[2.2.1]hept-5-ene-2,3-dicarboxylic anhydride) with benzylamine.

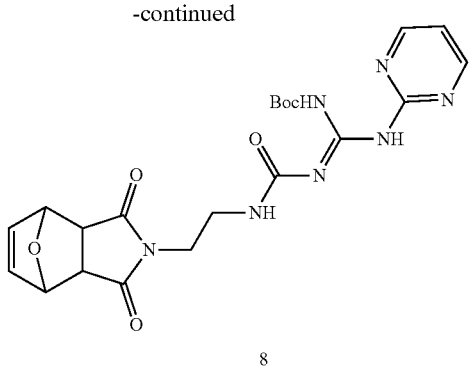

8

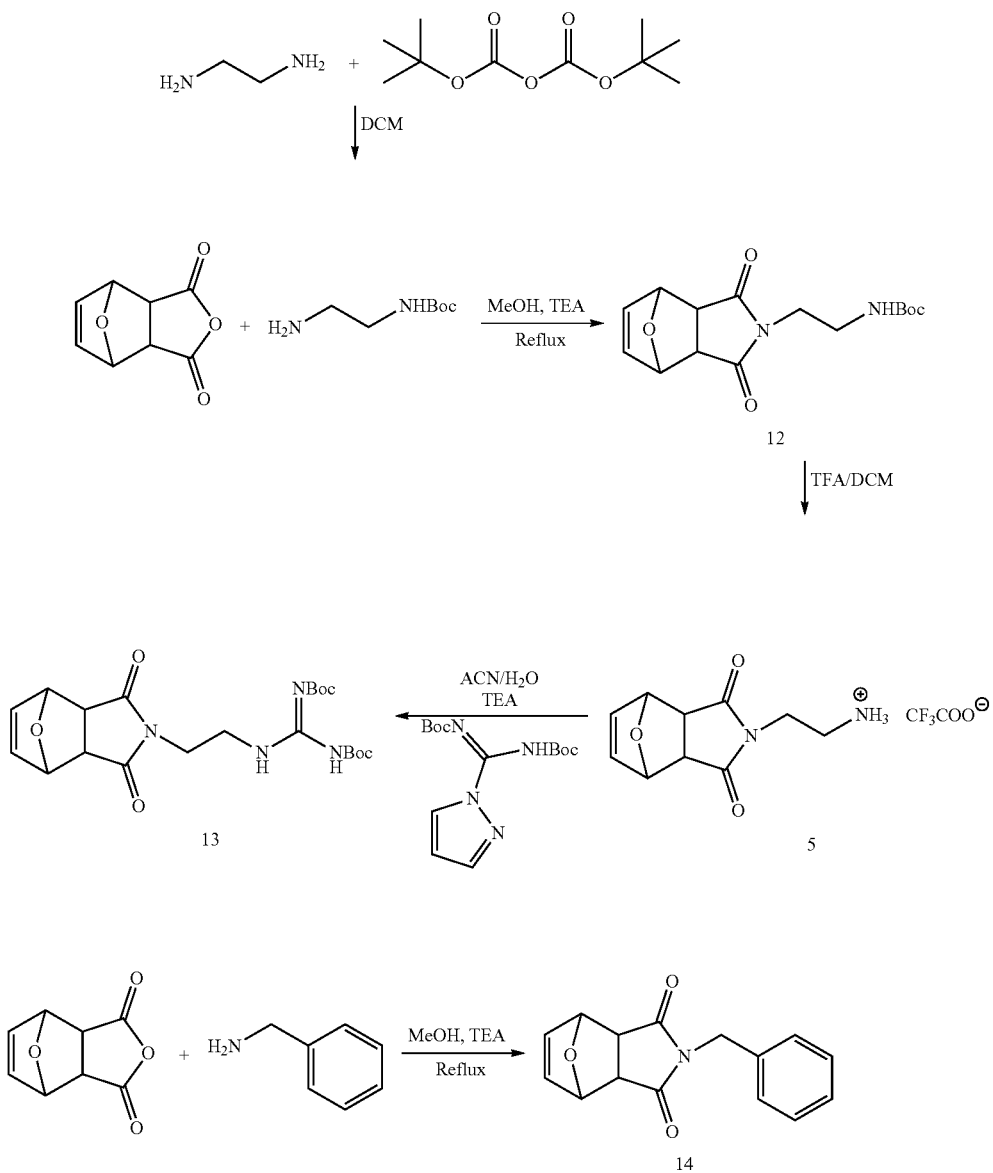

Scheme 10. Synthesis of monomers 13 and 14.

N-Boc protected ethylenediamine: Yield: 83%. $^1$H NMR (400 MHz, CDCl$_3$): δ 5.44 (br s, 1H), 2.96 (s, 2H), 2.59 (t, 2H), 1.25 (s, 9H), 1.04 (s, 2H). Compound 12: Yield: 50%. $^1$H NMR (400 MHz, CDCl$_3$): δ 6.51 (d, 2H), 5.25 (d, 2H), 4.79 (br s, 1H), 3.62 (t, 2H), 3.29 (t, 2H), 2.84 (t, 2H), 1.41 (s, 9H). Compound 5: Yield: 85%. $^1$H NMR (400 MHz, DMSO-d$_6$): δ 7.98 (s, 3H), 6.56 (s, 2H), 5.14 (s, 2H), 3.62 (t, 2H), 2.94 (m, 4H). Compound 13: Yield: 68%. $^1$H NMR (400 MHz, CDCl$_3$): δ 11.40 (s, 1H), 8.39 (s, 1H), 6.48 (d, 2H), 5.23 (d, 2H), 3.67 (t, 2H), 3.60 (t, 2H), 2.84 (t, 2H), 1.44 (m, 18H). Compound 14: Yield: 70%. $^1$H NMR (400 MHz, CDCl$_3$): δ 7.30 (m, 5H), 6.52 (s, 2H), 5.29 (s, 2H), 4.64 (s, 2H), 2.86 (s, 2H).

taken for GPC and NMR analysis. Finally, Boc-group on each polymer was removed using a mixture of methylene chloride and trifluoro acetic acid. After deprotection, deprotected polymers were precipitated (3 times) into diethyl ether and precipitated were collected, dried, weighed and dissolved in DMSO.

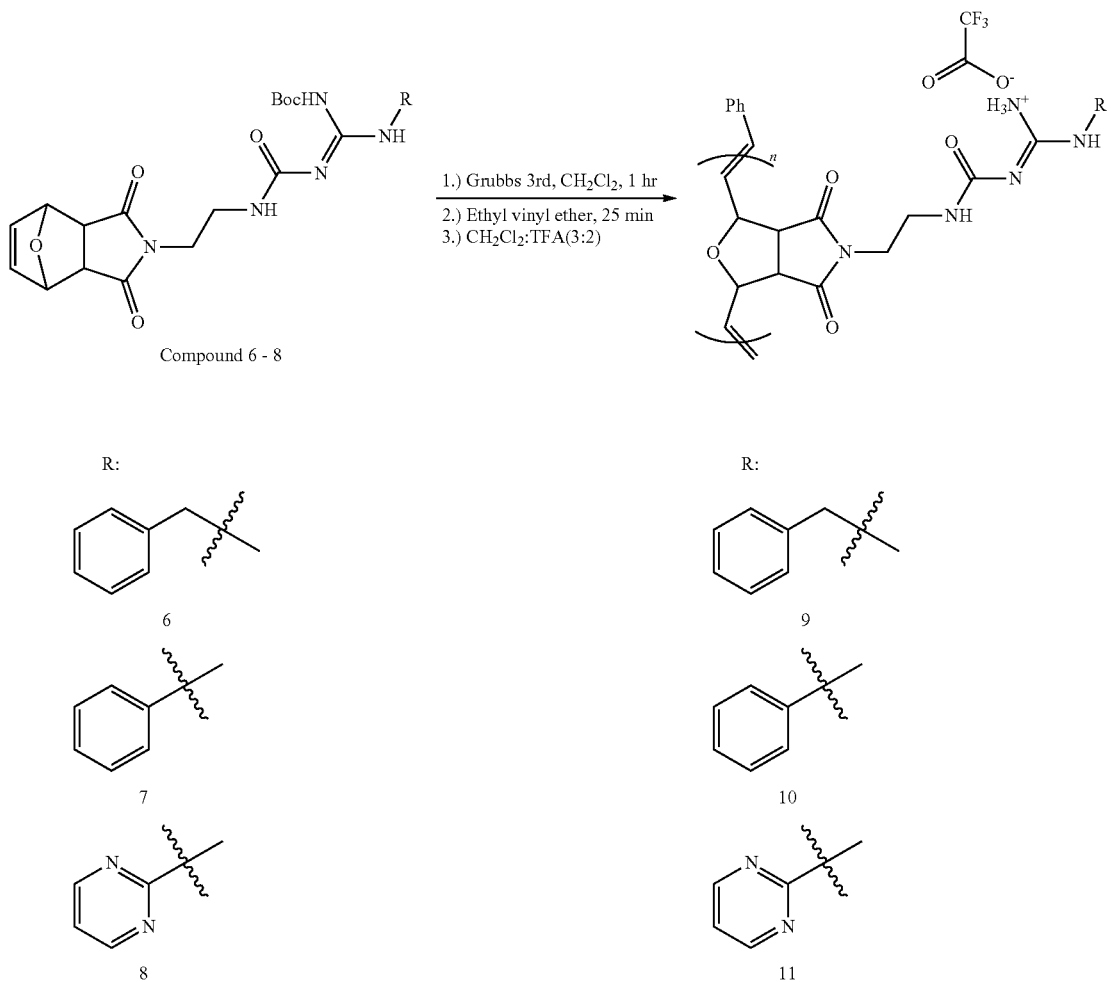

Scheme 11. ROMP of monomers 6, 7 and 8 using Grubbs catalyst 3$^{rd}$ Generation.

Synthesis of Polymers

N-Boc-N-(R)-Guanidyl Carbamoyl polymers were synthesized by dissolving monomer 6, 7 and 8 respectively in dry DCM and adding varying molar equivalents of Grubbs' 3$^{rd}$ generation catalyst (Scheme 11). The solutions were stirred for 1 hour before the addition of 500 uL of ethyl vinyl ether to terminate the polymerization. The polymer solutions were precipitated (3 times) into diethyl ether and precipitates were collected and dried. An aliquot of each polymer was

Synthesis of G

Scheme 12a shows the synthesis of G. Monomer 13 was dissolved in DCM. Grubbs 3$^{rd}$ generation catalyst was dissolved in DCM and added to the stirring monomer solution. After 60 min, the living polymer was end-capped with 1 mL of ethyl vinyl ether. The polymer solution was precipitated into stirring diethyl ether (3×) and dried. The dried solid was dissolved in a DCM/TFA mixture (1:1, v/v) and deprotected overnight. The reaction mixture was precipitated (3×) and collected via centrifugation.

G protected: $^1$H NMR (400 MHz, CDCl$_3$): δ 11.45 (br, 1H), 8.46 (br, 1H), 6.06 (br, 1H), 5.73 (br, 1H), 4.98 (br, 1H), 4.48 (br, 1H), 3.65 (br, 4H), 3.35 (br, 2H), 1.47 (d, 18H). G: $^1$H NMR (400 MHz, DMSO-d6): δ 7.97 (br, 1H), 7.42 (br, 4H), 5.97 (br, 1H), 5.76 (br, 1H), 4.94 (br, 1H), 4.45 (br, 1H), 3.51 (br, 2H), 3.34 (br, 4H).

Scheme 12a. Synthesis of polymers (G, and Ph-CG).

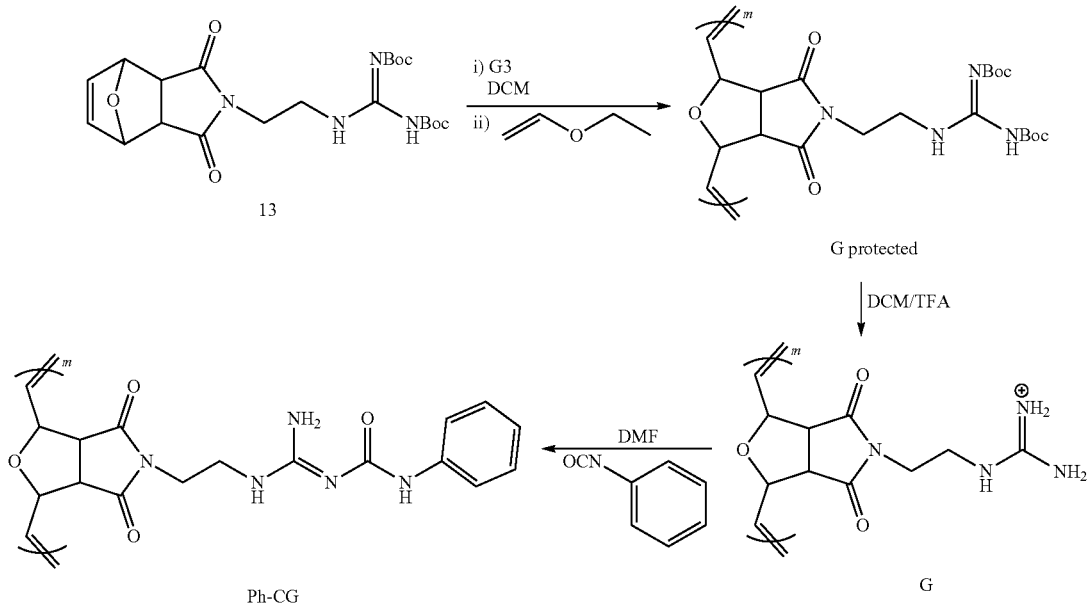

Synthesis of Ph-CG

Scheme 12a shows the synthesis of Ph-CG. G polymer was dissolved in dry DMF. 5 equivalents of phenyl isocyanate were added. The mixture was sealed in a vial and allowed to react overnight at 75° C. The reaction mixture was precipitated into diethyl ether (3×) and the polymer was collected via centrifugation. Ph-CG: $^1$H NMR (400 MHz, DMSO-d6): δ 7.94 (br, 2H), 7.43 (br, 3H), 7.27 (br, 2H), 5.92 (br, 1H), 5.71 (br, 1H), 4.87 (br, 1H), 4.42 (br, 2H), 3.41 (br, 6H).

Scheme 12b. Synthesis of polymers (Bz-CG, PhPr-CG, and PhBu-CG).

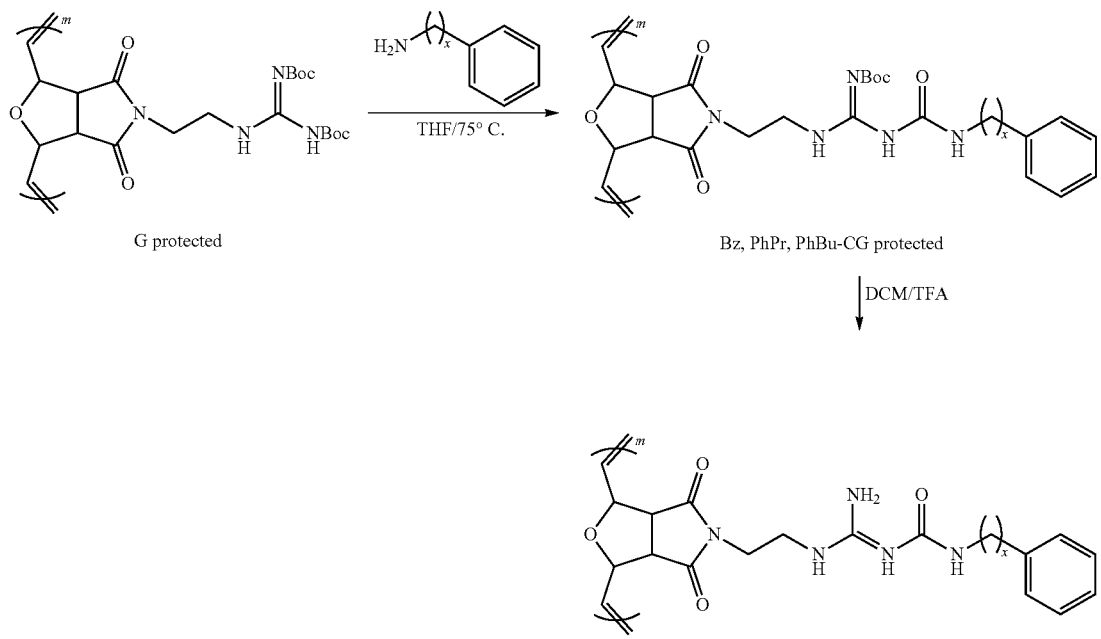

Synthesis of Bz, PhPr, and PhBu-CG

As shown in Scheme 12b, protected G polymer was dissolved in THF to which 2.5 equivalents of benzylamine, 3-Phenylpropylamine or 4-Phenylbutylamine were added. The mixture was sealed in a vial and allowed to react overnight at 75° C. The reaction mixture was precipitated into diethyl ether (3×) and then deprotected in DCM/TFA mixture (1:1, v/v). Deprotected polymer solution was precipitated into diethyl ether (3×) and polymer collected via centrifugation.

Bz-CG protected: $^1$H NMR (400 MHz, CDCl$_3$): δ 12.04 (br, 1H), 8.14 (br, 1H), 7.20 (br, 5H), 5.97 (br, 1H), 5.67 (br, 1H), 4.97 (br, 1H), 4.33 (br, 4H), 3.56 (br, 4H), 3.17 (br, 2H), 1.44 (s, 9H). Bz-CG: $^1$H NMR (400 MHz, DMSO-d6): δ 9.15 (br, 1H), 8.61 (br, 2H), 7.99 (br, 1H), 7.27 (br, 5H), 5.92 (br, 1H), 5.71 (br, 2H), 4.94 (br, 1H), 4.41 (br, 1H), 4.25 (br, 4H), 3.75 (br, 4H). PhPr-CG protected: $^1$H NMR (400 MHz, CDCl$_3$): δ 12.10 (br, 1H), 8.13 (br, 1H), 7.27 (br, 2H), 7.21 (br, 3H), 5.98 (br, 1H), 5.68 (br, 1H), 4.99 (br, 1H), 4.34 (br, 1H), 3.63 (br, 2H), 3.16 (br, 4H), 2.60 (br, 2H), 1.77 (br, 2H), 1.40 (s, 9H). PhPr-CG: $^1$H NMR (400 MHz, DMSO-d6): δ 9.18 (br, 1H), 8.14 (br, 2H), 7.94 (br, 1H), 7.21 (br, 5H), 5.97 (br, 1H), 5.65 (br, 1H), 4.82 (br, 1H), 4.36 (br, 1H), 3.64 (br, 2H), 3.18 (br, 4H), 2.58 (br, 2H), 1.76 (br, 2H). PhBu-CG protected: $^1$H NMR (400 MHz, CDCl$_3$): δ 12.08 (br, 1H), 8.08 (br, 1H), 7.27 (br, 2H), 7.10 (br, 3H), 6.02 (br, 1H), 5.71 (br, 1H), 5.06 (br, 1H), 4.34 (br, 1H), 3.66 (br, 2H), 3.14 (br, 4H), 2.59 (br, 2H), 1.60 (br, 4H), 1.40 (s, 9H). PhBu-CG: $^1$H NMR (400 MHz, DMSO-d6): δ 9.11 (br, 1H), 8.08 (br, 2H), 7.90 (br, 1H), 7.16 (br, 5H), 6.05 (br, 1H), 5.74 (br, 1H), 4.85 (br, 1H), 4.42 (br, 1H), 3.66 (br, 2H), 3.13 (br, 4H), 2.62 (br, 2H), 1.60 (br, 4H).

Synthesis of Random-Bz-G

As shown in Scheme 12c, molar equivalents of monomer 13 and 14 were dissolved in DCM. Grubbs 3$^{rd}$ generation catalyst was dissolved in DCM and added to the stirring monomer solution. After 60 min, the living polymer was end-capped with 1 mL of ethyl vinyl ether. The polymer solution was precipitated into stirring diethyl ether (3×) and dried. The dried solid was dissolved in a DCM/TFA mixture (1:1, v/v) and deprotected overnight. The reaction mixture was precipitated (3×) and collected via centrifugation.

Random-Bz-G protected: $^1$H NMR (400 MHz, CDCl$_3$): δ 11.43 (br, 0.5H), 8.46 (br, 0.5H), 7.27 (br, 2.5H), 6.04 (br, 1H), 5.75 (br, 1H), 4.99 (br, 1H), 4.64 (br, 1H), 4.47 (br, 1H), 3.65 (br, 2H), 3.32 (br, 2H), 1.44 (s, 9H). Random-PN-Bz-G: $^1$H NMR (400 MHz, DMSO-d6): δ 7.73 (br, 1H), 7.26 (br, 4H), 5.96 (br, 1H), 5.71 (br, 1H), 4.88 (br, 1H), 4.55 (br, 1H), 4.41 (br, 1H), 3.47 (br, 2H), 3.33 (br, 2H).

Scheme 12c. Synthesis of polymers (random-Bz-G).

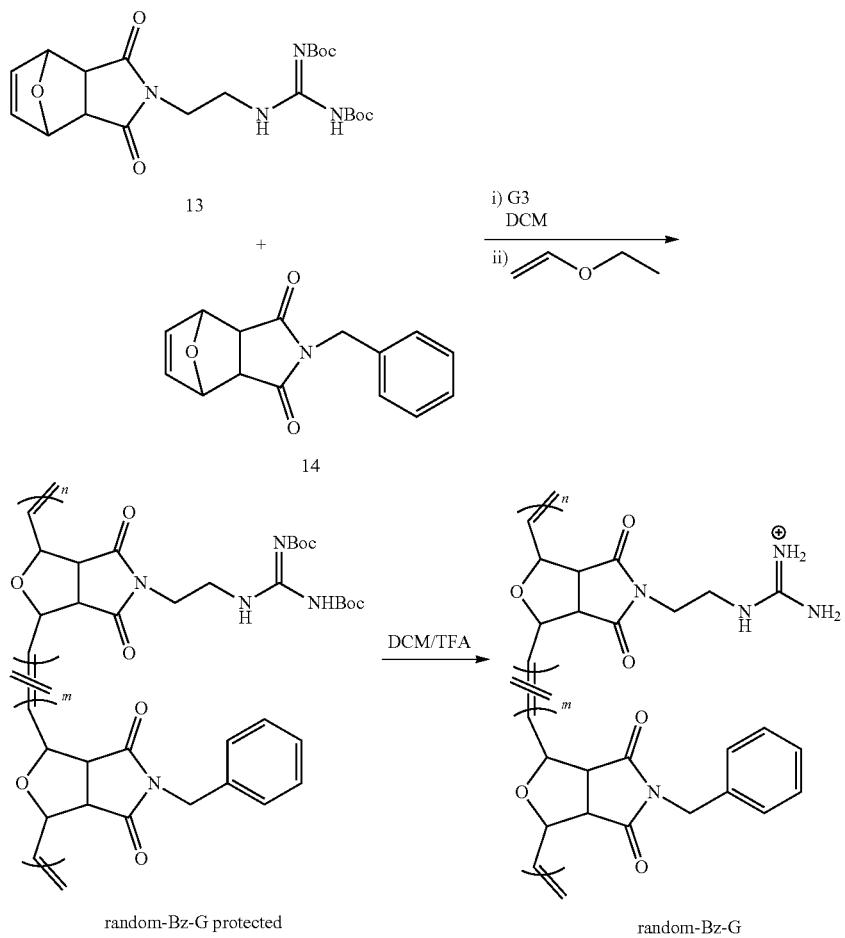

random-Bz-G protected      random-Bz-G

Scheme 12d. Synthesis of polymers (block-Bz-G).

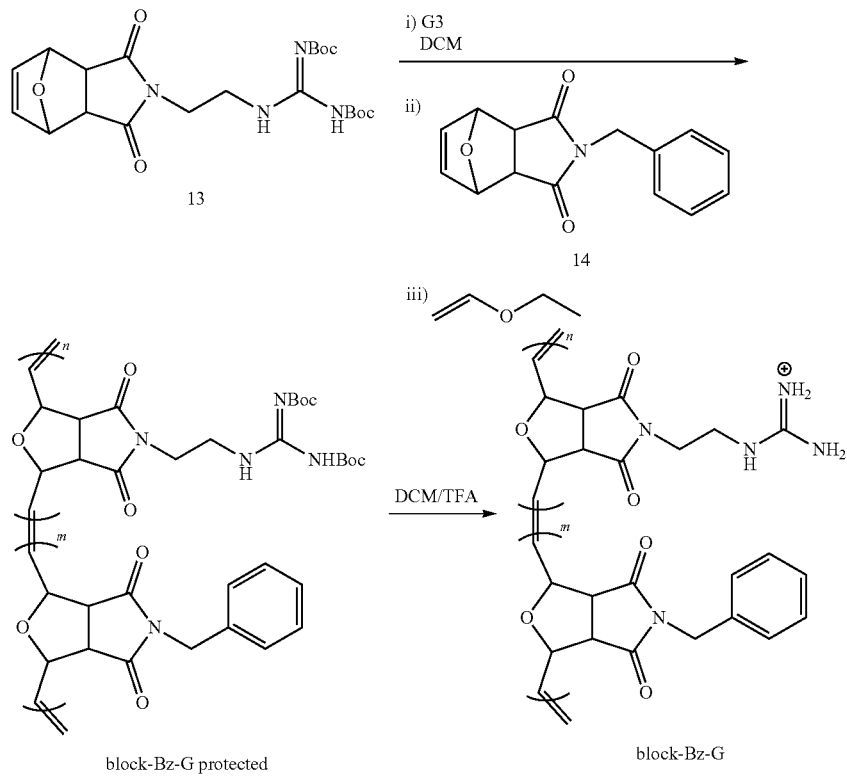

Synthesis of Block-Bz-G

As shown in Scheme 12d, monomer 13 was dissolved in DCM. Grubbs 3$^{rd}$ generation catalyst was dissolved in DCM and added to the stirring monomer solution. After 15 mins, monomer 14 solution was added to the stirring polymerization solution and allowed to stir for additional 45 mins. Afterwards, the living polymer was end-capped with 1 mL of ethyl vinyl ether. The polymer solution was precipitated into stirring diethyl ether (3×) and dried. The dried solid was dissolved in a DCM/TFA mixture (1:1, v/v) and deprotected overnight. The reaction mixture was precipitated (3×) and collected via centrifugation.

Block-Bz-G protected: $^1$H NMR (400 MHz, CDCl$_3$): δ 11.41 (br, 0.5H), 8.47 (br, 0.5H), 7.30 (br, 2.5H), 6.00 (br, 1H), 5.68 (br, 1H), 5.04 (br, 1H), 4.56 (br, 1H), 4.42 (br, 1H), 3.68 (br, 2H), 3.28 (br, 2H), 1.46 (s, 9H). Block-Bz-G: $^1$H NMR (400 MHz, DMSO-d6): δ 7.91 (br, 0.5H), 7.44 (br, 2H), 7.23 (br, 2.5H), 5.96 (br, 1H), 5.72 (br, 1H), 4.94 (br, 1H), 4.51 (br, 1H), 4.45 (br, 1H), 3.46 (br, 2H), 3.35 (br, 2H).

Molecular Weight Determination

Aliquots of polymer solutions in tetrahydrofuran (THF) or dichloromethane (DCM) were diluted in 1 mL of HPLC-grade THF and filtered through a 0.45 μm polytetrafluoroethylene (PTFE) syringe filter prior to injection.

Measurement of Hydrodynamic Diameters and Zeta Potential

Nanoparticle tracking analysis (NTA) was used to determine the hydrodynamic diameter (HD) of PN/protein complexes. Briefly, 1 mL of PN/BSA complexes with final concentrations of 10 μM/100 nM were prepared by mixing equal volumes of polymer and BSA substock solutions, incubating for 30 minutes and diluting in PBS to a final volume of 1 mL. 1 mL of this solution was then injected into the NTA chamber and videos of the scattering particles was recorded for 30 seconds. The software identified each individual particle and tracked its motion, relating the particle displacement as a function of Brownian motion, which relates to the particle size through the Stokes-Einstein equation. The concentrations of samples were chosen to meet the manufacturers' recommendation of 20-100 particles per frame and a concentration of $10^7$-$10^9$ particles/mL. All measurements were performed in triplicate at 25° C. One representative HD plot was selected for Ph-CG/BSA complex (10 μM/100 nM), demonstrating the formation of monodisperse nanoparticles. Zeta Potential was acquired by preparing samples in the same way as for NTA prior to analysis.

pKa Determination pKa was determined for the different PNs by titrating 2 mM polymer solution in 1 mL of acidified (pH~3) 100 mM NaCl solution and titrating to pH 11 with 5 μL increments of a 25 mM KOH solution. For the titration, the pH was determined using a Mettler Toledo InLab Ultra-Micro pH Probe. pKa value for each polymer was determined by plotting the ΔpH/volume of KOH (FIG. 3A) and identifying the largest ΔpH. For polymers with two maxima, the volume of the median point between the two maxima was chosen as the point where pH=pKa. For random-Bz-G (FIG. 3C) and block-Bz-G, no deprotonation of the cationic moiety occurs and therefore titration curves are only representative of the change in pH of solution.

Fluorescent Quenching Titration

The complexation between the PNs and protein was studied by monitoring the fluorescence emission intensity (Ex: 540 nm; Em: 576 nm) of rhodamine-labelled bovine serum albumin (Rho-BSA) as a functional of increasing concentrations of PNs. Rhodamine quenching was indicative of protein binding. Briefly, polymer solutions in DMSO were serially diluted in DMSO and further diluted in $H_2O$. Emission of Rho-BSA solutions was taken before and after the addition of polymer solutions, and the relative emission intensity as a function of polymer concentration was plotted. Final concentration of Rho-BSA was 100 nM and of polymers ranged from 32-0.5 µM.

Dissociation Constant Determination

The dissociation constant was determined by converting the relative fluorescence quenching plots to fractional saturation plots using equation 1 below:

$$\text{Fractional Saturation}(y) = \frac{F_P - F_0}{F_{sat} - F_0} \quad (1)$$

where $F_0$, $F_P$, and $F_{sat}$ were the relative emission intensities of Rho-BSA only, polymer/Rho-BSA complexes at the various concentrations tested, and polymer/Rho-BSA at saturation. The dissociation constant was determined by equation 2 below:

$$y = \frac{(P + c + K_d) - \sqrt{(P + c + K_d)^2 - 4Pc}}{4c} \quad (2)$$

where y is the fractional saturation plot obtained with equation 1, P is the polymer concentration (x-axis) and c is the constant Rho-BSA concentration (100 nM). $K_d$ was determined using the non-linear curve fitting module of Origin 8.5 and equation 2.

Serum Stability Assay

The stability of complexes in the presence of 10% fetal bovine serum (FBS) was studied by monitoring the fluorescence of PN/Rho-BSA complexes over 2 hours. Briefly, 40 µL of complexes were prepared by mixing equal volumes of polymer and Rho-BSA solutions and allowing them to complex for 30 m. These complexes were then diluted into 360 µL of either PBS or PBS with 10% FBS and the emission spectra was recorded immediately. The complexes were allowed to sit at room temperature between readings.

Cell Culture

HeLa cells were cultured in Gibco DMEM High Glucose medium supplemented with 10% (v/v) FBS and 1% (v/v) Penicillin-Streptomycin mixture. Adipose derived mesenchymal stem cells and T cells were a kind gift from Dr. Robert Sackstein at Florida International University. MSCs were cultured in DMEM high glucose medium supplemented with 10% FBS and then treated with PN/R-PE. T cells were cultured in RPMI supplemented with 10% FBS and then treated with PN/R-PE.

PN Toxicity Assay

HeLa cells were seeded in a 96-well plate (~10,000/well) in 200 µL of complete medium and allowed to attach for one day at 37° C. under a humidified atmosphere of 5% $CO_2$ prior to sample treatment. Final concentrations of 40, 20, 10, and 5 µM were added into the complete media by dilution of the polymer stock solutions. After addition of the samples, cells were incubated for 18 h prior to treatment with 10 µL of methylthiazole tetrazolium (MTT) (5 mg/mL in PBS) and incubated for 4 h at 37° C. After incubation, 200 µL of medium was gently removed and 100 µL of biological grade DMSO was added to solubilize the purple formazan crystals. Absorbance was measured by microwell plate reader. Cell viability was determined as a function of absorbance of each sample relative to control wells. All measurements represent the average of three independent measurements+/−standard deviation.

Flow Cytometry Analysis

Hela cells and MSCs were seeded into 12 or 6-well plates (~100,000/well or 60,000/well, respectively) in complete media and allowed to attach for one day at 37° C. under a humidified atmosphere of 5% $CO_2$ prior to sample treatment. In contrast, T-cells were counted plated in 12-well plates (~400,000/well) in complete RPMI media and treated right away. R-PE, EGFP, FITC-BSA, and Rho-BSA stock solutions were diluted to working concentrations with 1×PBS. Polymer stock solutions were prepared at 1 mM in DMSO. 40 µL of polymer/protein complexes were prepared by mixing appropriate volumes of polymer and protein substock solutions and incubating for 30 m at room temperature in the dark. Complexes were added dropwise to each well to the cells in complete media and incubated for varying periods of time, depending on the experiment. After the incubation periods required, adherent cells were rinsed three times with full volumes of PBS, followed by washing with 1 µM heparan sulfate solution to remove any extracellular surface-bound complexes. The cells were harvested with TrypLE, transferred to centrifuge tubes, rinsed an additional three times with PBS before being finally resuspended in 300 µL of PBS. In the case of suspension cells, cells were transferred to centrifuge tubes, centrifuged and resuspended in PBS three times. Cells were analyzed by flow cytometry, in which data for 10,000 events were collected. Analysis for primary cells were performed with supervision and technical assistance of Dr. Sackstein group.

Cellular Entry Pathway

In order to study the mechanism of uptake, HeLa cells were treated with Ph-CG/R-PE complexes (10 µM/15 nM) for 1 h under energy-independent conditions or under pretreatment with various pharmacological inhibitors. Briefly, HeLa cells seeded the day prior to sample treatment in 12-well plates (100,000/well). The day of experiment, cells were equilibrated for 30 minutes under 4° C., ATP depletion conditions ($NaN_3$: 10 mM & 2-deoxyglucose: 50 mM), chlorpromazine (28 µM), LYS 294003 (3 µM), Cytochalastin D (10 µM), methyl-B-cyclodextrin (1 mM) and genistein (200 µM) or normal culture conditions. Complexes were added dropwise, and cells were incubated for 1 h prior to analysis via flow cytometry as described previously.

Functional Protein Delivery

MTT assay was performed with PN/enzyme complexes are described previously. In short, serial dilutions of saporin or RNase were prepared and complexes with various PNs. For serum-containing media, complexes were added to HeLa cells and incubated overnight prior to MTT treatment. For serum-free experiments, complexes were added in DMEM for 4 h and the media was replaced with complete media overnight prior to MTT treatment.

Confocal Imaging

Hela cells were seeded on 12-well plates (~60,000/well) containing glass coverslips one day before sample treatment. Complexes were prepared as described previously. After incubation for varying periods of time using same culture conditions discussed earlier, the medium was removed, and cells were washed three times with PBS and once with heparan sulfate. Cells were fixed with 4% PFA for 10 minutes and rinsed once with PBS. Nuclei were stained with Hoechst 33342 at final concentration of 1 µg/mL for 7 minutes. For cells with Lysotracker Red staining, the manufacturers protocol was followed. The coverslips were mounted on microscope slides using 1:1 glycerol/PBS mounting medium.

Example 1—Characterizations of PNs and PN/BSA Complexes

After synthesizing a guanidine containing poly(oxanorbornene imide) (G, FIG. 1), phenyl isocyanate was reacted with guanidine to synthesize the Ph-CG containing PN. Synthesis of Bz, PhPr, and PhBu was done via the reaction of the respective primary amines and the N,N'-di-boc-guanidine containing PN. Random and block copolymers with repeating units bearing both guanidine and aromatic benzyl side chains (random-Bz-G and block-Bz-G) were also synthesized as control PNs (Schemes 10 and 12).

Figure 2:
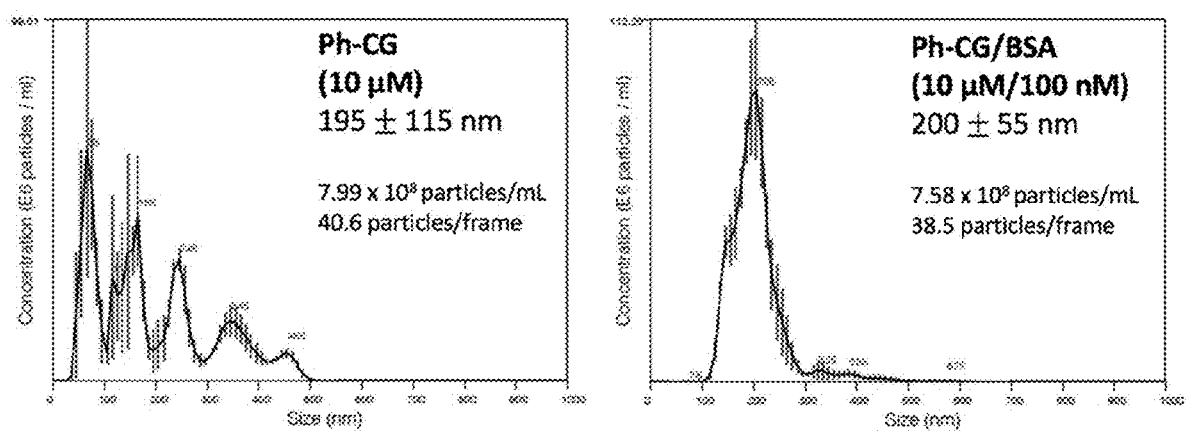
FIG. 2 shows representative HD plots for Ph-CG (left) and Ph-CG/BSA complex (right), demonstrating formation of relatively monodisperse nanoparticles after complexation.

Complexation was achieved by mixing the corresponding PN and protein in an aqueous solution. Nanoparticle tracking analysis and zeta potential measurements indicate that all PNs form relatively uniform nanometer size complexes with slightly negative zeta potentials (FIG. 2), despite the excess amounts of PNs used in the complex (Tables 1 and 2).

TABLE 1

Summary of molecular weights ($M_n$ and $M_w$, kDa) and acidity constant (pKa) of polymers and the hydrodynamic diameters (HD, nm), zeta potentials ($\zeta$), and dissociation constants ($K_d$, μM) of PN/BSA complexes.

| PNs | $M_n$ | $M_w$ | HD[a] | $\zeta$[a] | $K_d$[b] | $pK_a$[c] |
|---|---|---|---|---|---|---|
| G | 4.8 | 5.4 | NA | NA | NA | NA |
| Ph-CG | 5.5 | 5.9 | 200 ± 55 | −14.3 | 3.7 ± 0.8 | 6.1 |
| Bz-CG | 5.7 | 6.1 | 179 ± 31 | −15.3 | 3.8 ± 0.6 | 6.1 |
| random-Bz-G | 5.0 | 5.6 | 230 ± 50 | −8.9 | 3.3 ± 0.6 | NA |
| block-Bz-G | 4.5 | 5.1 | 178 ± 45 | −6.1 | 5.3 ± 1.3 | NA |

[a]Concentrations of polymer and BSA in the complexes were 10 μM and 100 nM, respectively.
[b]Dissociation constants were calculated using rhodamine labelled BSA.
[c]Effective $pK_a$ was determined by pH titration.
NA: Not able to determine under the titration condition.

TABLE 2

Summary of molecular weights ($M_n$ and $M_w$, kDa) and acidity constant (pKa) of polymers and the hydrodynamic diameters (HD, nm), zeta potentials ($\zeta$), and dissociation constants ($K_d$, μM) of PN/BSA complexes.

| PNs | $M_n$ | $M_w$ | HD[a] | $\zeta$[a] | $K_d$[b] | $pK_a$[c] |
|---|---|---|---|---|---|---|
| PhPr-CG | 5.7 | 6.1 | 168 ± 44 | −11.6 | 3.1 ± 0.4 | 6.3 |
| PhBu-CG | 5.7 | 6.1 | 175 ± 36 | −13.4 | 5.7 ± 1.2 | 6.1 |
| random-Bz-G (10 k) | 10.3 | 11.4 | 208 ± 54 | −11.9 | — | NA |
| block-Bz-G (10 k) | 8.9 | 10.3 | 209 ± 48 | −14.5 | — | NA |

[a]Concentrations of polymer and BSA in the complexes were 10 μM and 100 nM, respectively.
[b]Dissociation constants were calculated using rhodamine labelled BSA.
[c]Effective $pK_a$ was determined by pH titration.
NA: Not able to determine under the titration condition.

Considering the negatively charged bovine serum albumin (BSA) in neutral pH, the negative zeta potentials of PN/BSA complexes suggest the possible neutral (or slightly positive) charge of PNs, especially for Ph-CG. The acylation on guanidine results in a sharp pKa decrease from 12-13 to ~8. The pKa values of CG derivatives were measured as ~6.1 using the pH titration method (FIG. 3). Therefore, Ph-CG exists as neutral in the physiological environment.

Figure 4:
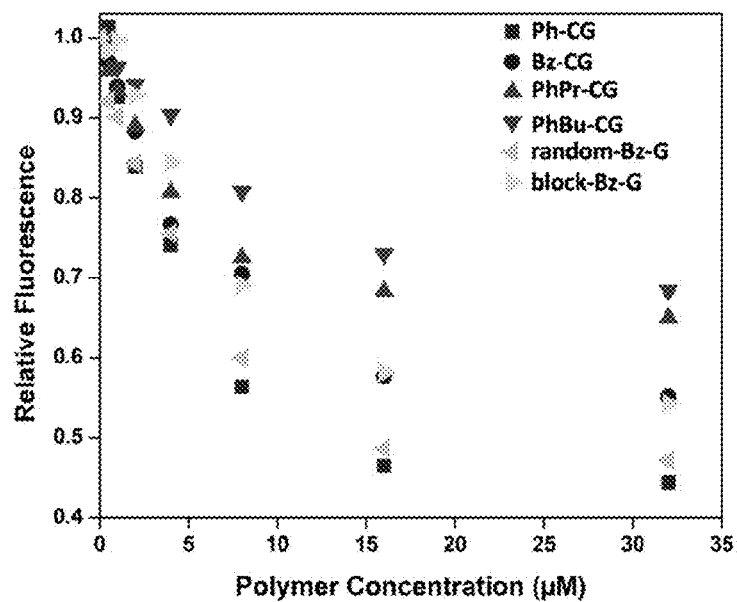
FIG. 4 shows the relative fluorescent quenching of Rho-BSA complexed with various PNs. Data represents the average of 3 independent experiments. Errors bars were omitted for clarity of data.
Figure 5:
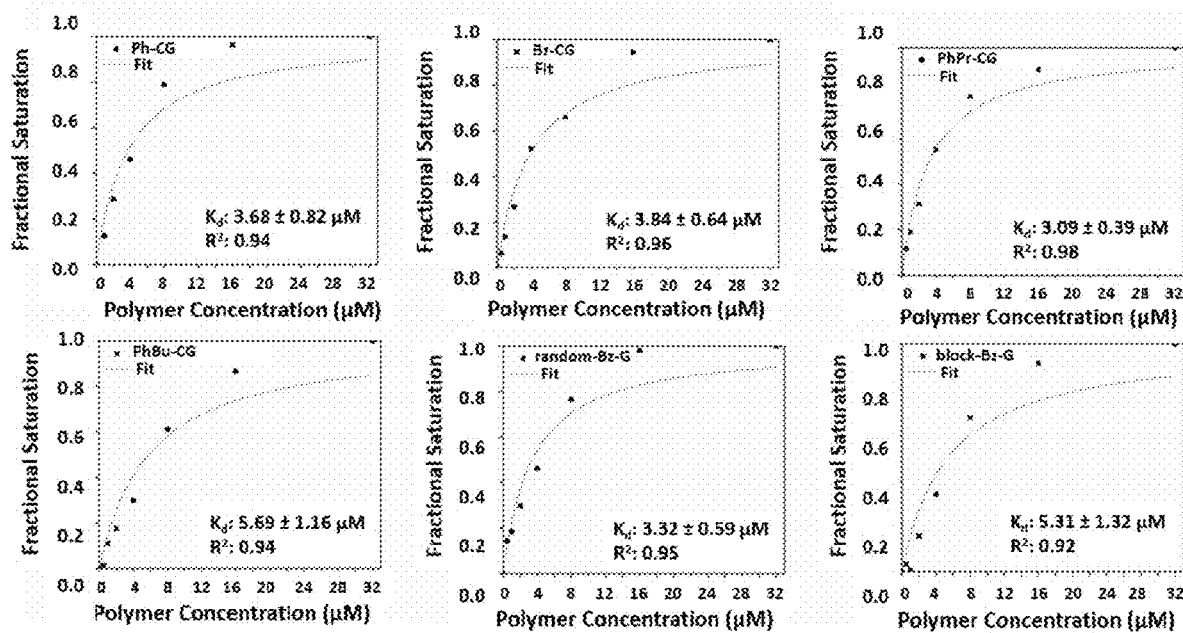
FIG. 5 shows fractional saturation and fitting curves of PNs with Rho-BSA.
Figures 6A, 6B:
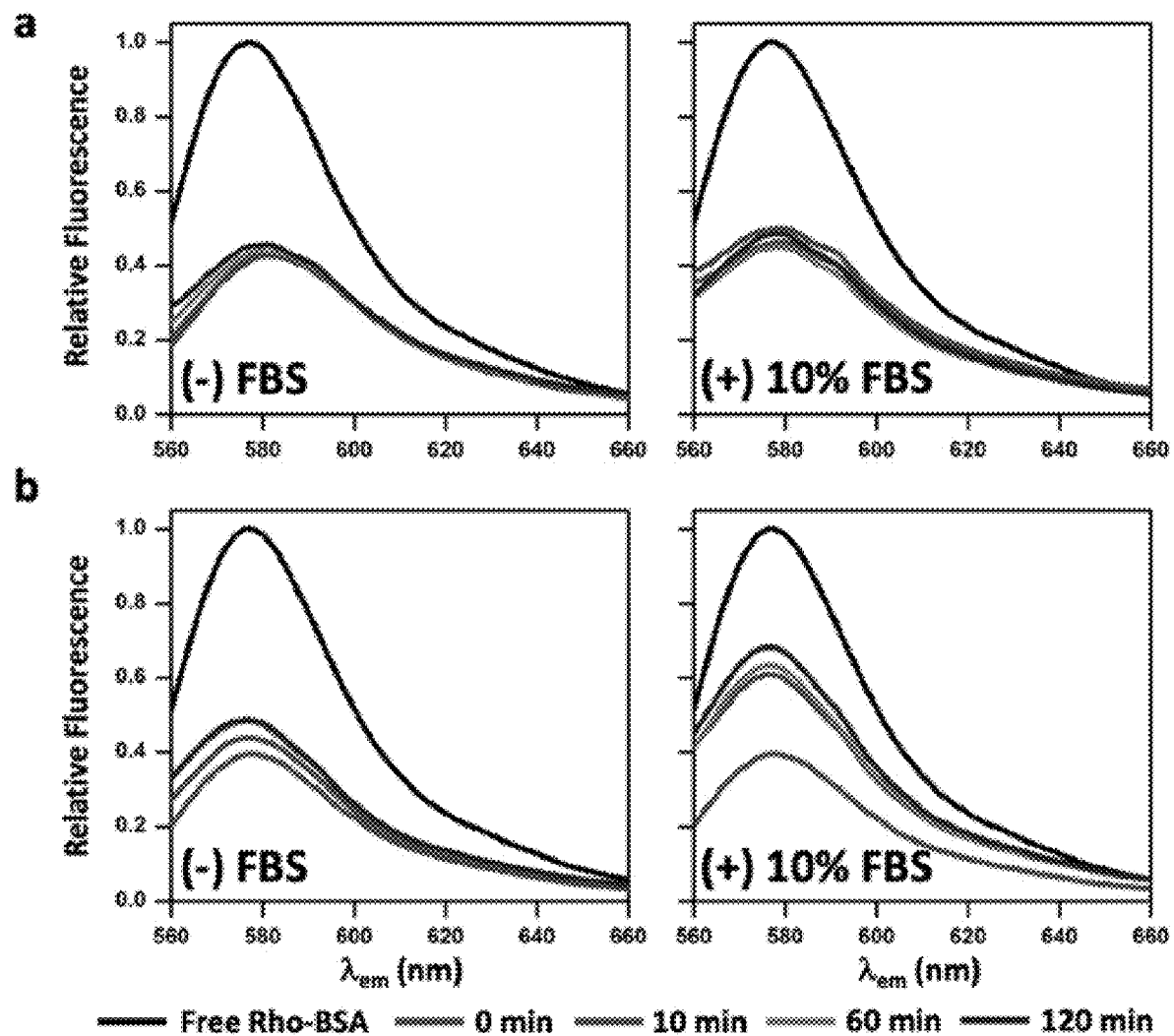
FIGS. 6A-6B show stability of protein complexes of (6A) Ph-CG and (6B) random-Bz-G in PBS (left) and PBS containing 10% FBS (right). While both Ph-CG and random-Bz-G complexes show a relatively good stability in PBS, the complex stability in the serum-containing medium is substantially different. Ph-CG/protein complex exhibits high serum stability over the extended incubation time.
Figure 7:
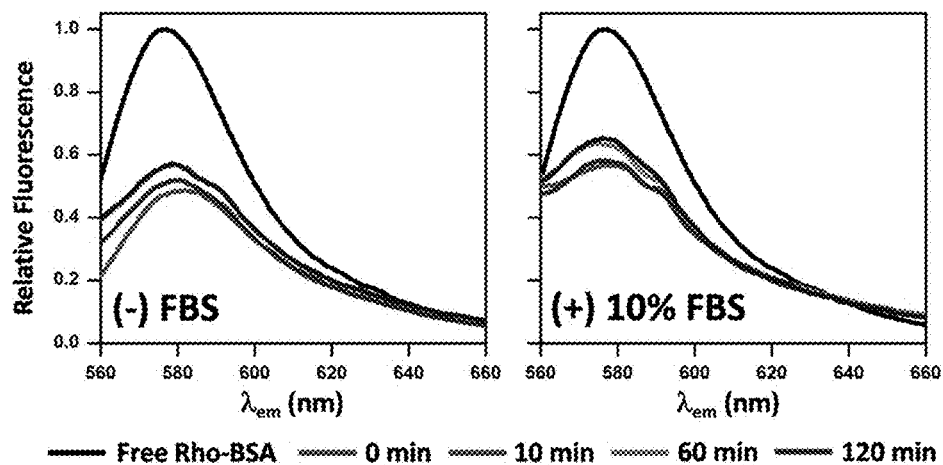
FIG. 7 shows the stability of Bz-CG/Rho-BSA complexes in PBS (left) and PBS containing 10% FBS (right).

Fluorescence quenching assays using rhodamine-labeled BSA (Rho-BSA) confirm the high protein affinity of Ph-CG. The fluorescence intensity of Rho-BSA will be decreased as the Rho-BSA concentration increases in the complex due to self-quenching. By monitoring the fluorescence quenching of Rho-BSA as a function of PN concentrations, the dissociation constants ($K_d$) of PN/BSA complexes were determined as ~3-5 μM (FIGS. 4 and 5). Despite very similar $K_d$ values, the complex stability in phosphate buffered saline (PBS) containing 10% fetal bovine serum (FBS) is significantly different depending on the functional group. While the Ph-CG/protein complex exhibits the same fluorescence intensity to that of the initial complex, the random-Bz-G/protein complex shows a slight increase in the intensity within the 2 h of incubation in a serum free medium (FIGS. 6A-6B). In the presence of serum, the Ph-CG/complex exhibits no fluorescence changes over the incubation time (FIG. 6A), indicating the complex stability was not compromised by the serum proteins. Meanwhile, the fluorescence intensity of random-Bz-G/protein complex was sharply increased within 10 min of incubation (FIG. 6B), suggesting the substantial complex dissociation. Another CbmG derivative, Bz-CG, also exhibits excellent serum stability similarly to Ph-CG (FIG. 7).

Considering the similar physical properties of the PN/protein complexes, this substantial serum stability difference between CbmG- and conventional guanidine-containing PNs is due to enhanced HB interactions of CbmG resulted from low pKa value and attached hydrophobicity.

Example 2—Cellular Delivery Efficiencies

Figure 8:
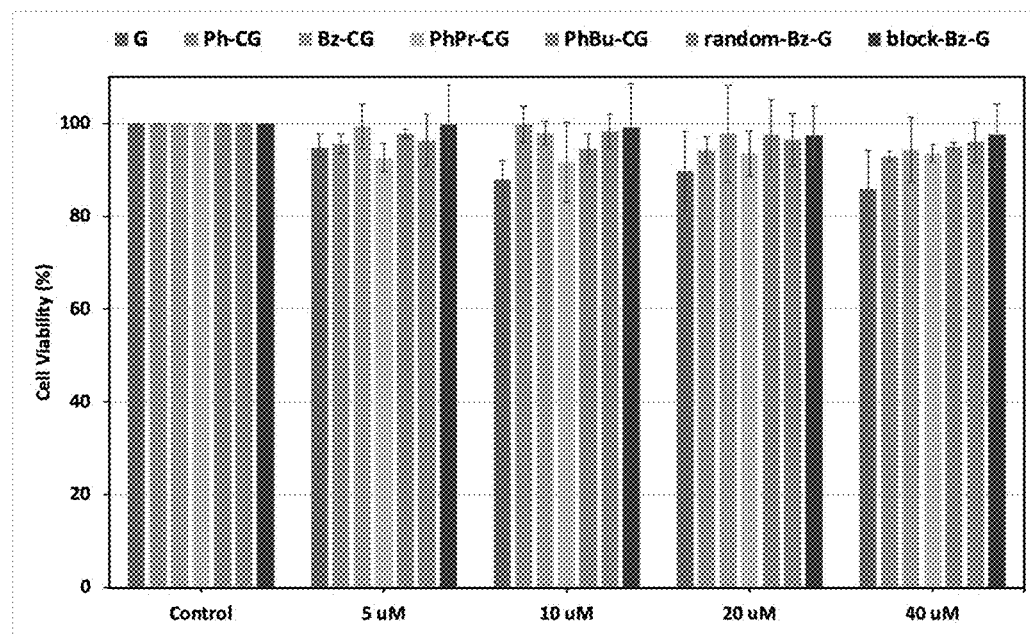
FIG. 8 shows the cell viability inhibition of PNs at various concentrations.

All PNs exhibited no noticeable cell viability inhibition up to 40 mM, except the guanidine containing PN (G) that showed a slight viability inhibition (~15%) at that concentration (FIG. 8).

Figure 9:
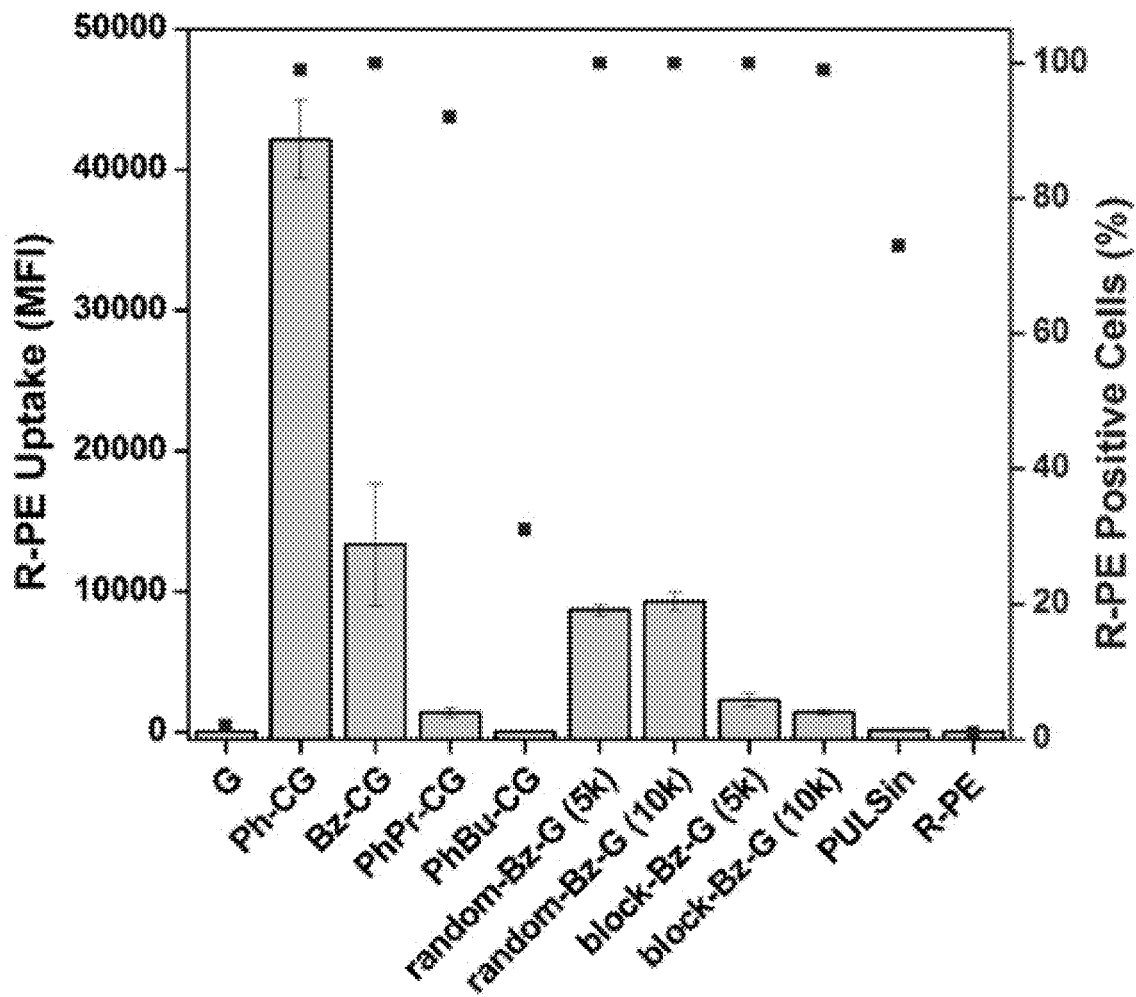
FIG. 9 shows the median fluorescence intensity of HeLa cells treated with PN/R-PE complexes for 18 h. The percent R-PE positive cells are presented at the right axis. The concentration of polymer and R-PE were 10 μM and 15 nM, respectively. R-PE only was used as a negative control. PULSin was used as a positive control according to suggested guidelines by the manufacturer. Data shown is the mean of three independent experiments+/−standard deviation.

Using flow cytometry, the cellular protein delivery efficiencies of PNs were evaluated by measuring the median fluorescent intensity (MFI) of HeLa cells incubated with PNs/red algae-phycoerythrin (R-PE) complexes in a serum-containing medium overnight. As shown in FIG. 9, Ph-CG with molecular weight (MW) of ~5,000 g/mol exhibits about 5- and 300-fold higher MFI than the control random-Bz-G and the commercially available PULSin reagent, respectively, despite all PN/R-PE treated cells being R-Pe positive.

Structurally, the hydrophobic phenyl group is directly introduced to guanidine via the Cbm extension in Ph-CG, whereas the charges and hydrophobic groups in the control PNs are segregated in either random or block backbone structures. The control PNs with doubled MWs, in which the PNs have the same numbers of guanidine and hydrophobic unit per repeating unit to those of Ph-CG, exhibit no improved delivery efficiency. It is interesting to observe that the R-PE delivery efficiency decreases exponentially as the chain length between Ph and CG increases (FIG. 9). The separation of the phenyl ring by 1 carbon unit (i.e., Bz-CG) decreases the protein uptake efficiency by ~75% and a further increase in the distance (i.e., PhPr and PhBu) eventually leads to minimal delivery.

Considering very similar pKa, fluorescence quenching behaviours, and complex serum stability among the CG derivatives, it is believed that the coplanarity of Ph-CG contributes to better cellular entry through better interactions with the membranes, resulting in high protein delivery efficiency. While the Ph group maintains the coplanarity with CG through p-electron conjugation in Ph-CG and thus the rigidity of the active group is maintained, no coplanarity is present when the phenyl group is connected to Cbm through methylene spacers because of free rotation of the methylene group.

Example 3—Cellular Delivery Using Ph-CG

Figure 10:
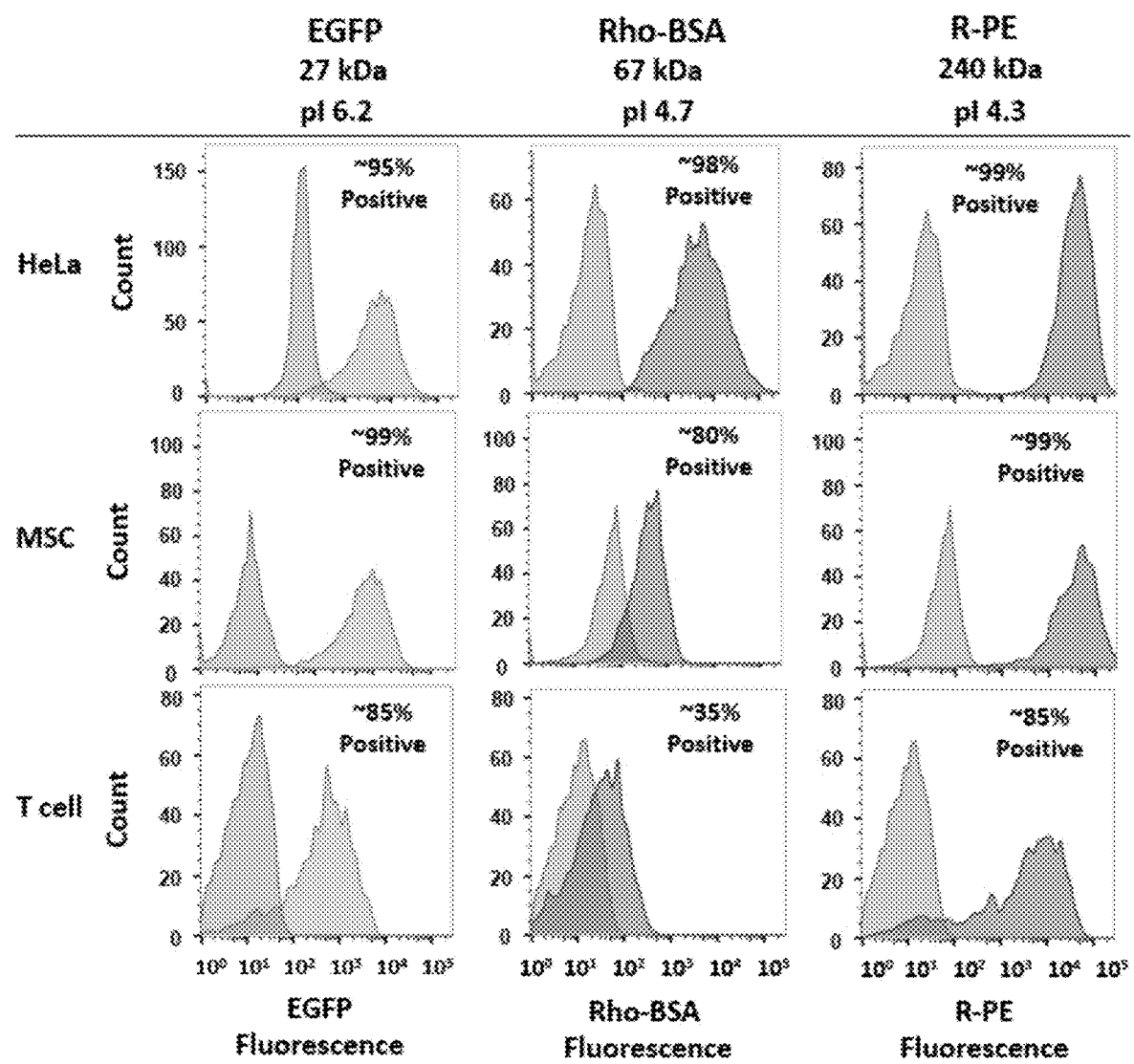
FIG. 10 shows flow cytometry histograms of Ph-CG mediated delivery of EGFP, Rho-BSA and R-PE into HeLa, Mesenchymal Stem Cells (MSC), and T cells. Almost complete cell populations show signals from R-PE within 3 h of treatment. The concentrations of polymer, R-PE, EGFP, and Rho-BSA were 10 μM, 15 nM, 60 nM, and 100 nM, respectively.

The robust design concept of Ph-CG for universal protein delivery was examined by treating primary human mesenchymal stem cells (MSC) and CD4+ T cells, respectively, with Ph-CG/fluorescent proteins (FPs) in serum containing media. As shown in FIG. 10, Ph-CG efficiently delivers various FPs with different sizes and surface properties to hard-to-transfect cells with greater than 80% of the FP positive cell populations.

Interestingly, Rho-BSA delivery efficiency was generally lower than that of the intrinsic FPs. It is speculated that the altered surface functionalities from chemical conjugations of Rho to BSA could be responsible for the relatively low delivery efficiency. For those non-FPs with smaller size (e.g., 13.7 kDa RNase A) and positively charged surfaces [i.e., RNase (pI 8.6) and Saporin (pI 9.3)], functional assays were used to validate Ph-CG-mediated delivery in a serum containing medium.

Figure 11:
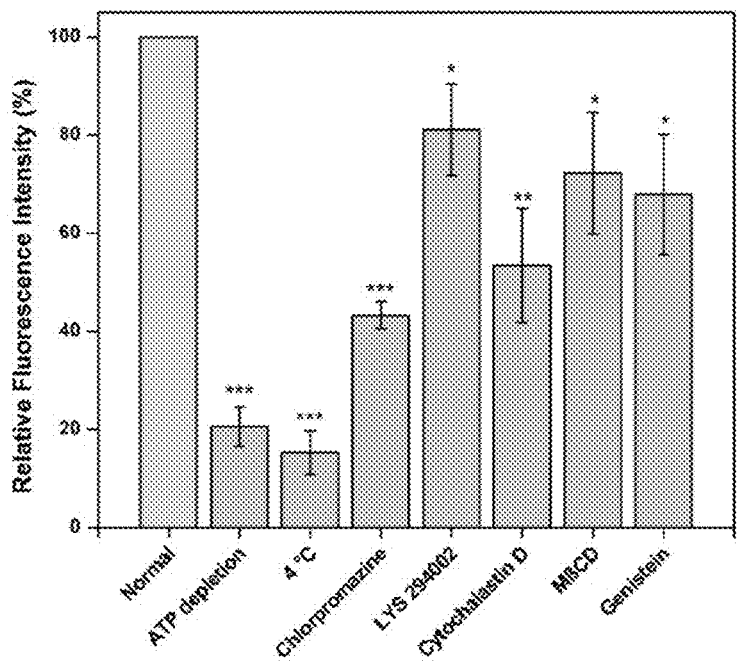
FIG. 11 shows the relative median fluorescence intensity of HeLa cells in energy-independent conditions (ATP depletion and 4° C.) or pre-treated with various pharmacological endocytosis inhibitors followed by incubation with Ph-CG/R-PE complex for 1 h. The concentration of polymer and R-PE were 10 μM and 15 nM, respectively. Data shown is the mean of three independent experiments+/−standard deviation. *p<0.05, p<0.01, and *p<0.001.

Cellular entry pathway studies indicate that the internalization of the Ph-CG/R-PE complex primarily occurs via energy dependent pathway (FIG. 11). Ph-CG/R-Pe entry was decreased under the pretreatment of various pharmacological endocytosis inhibitors, implying that those relatively well-studied endocytosis pathways (i.e., clathrin-mediated endocytosis and macropinocytosis) are also involved in Ph-CG/FPs entry to HeLa cells.

Example 4-pH-CG for Functional Enzyme Delivery

Figures 12A, 12B:
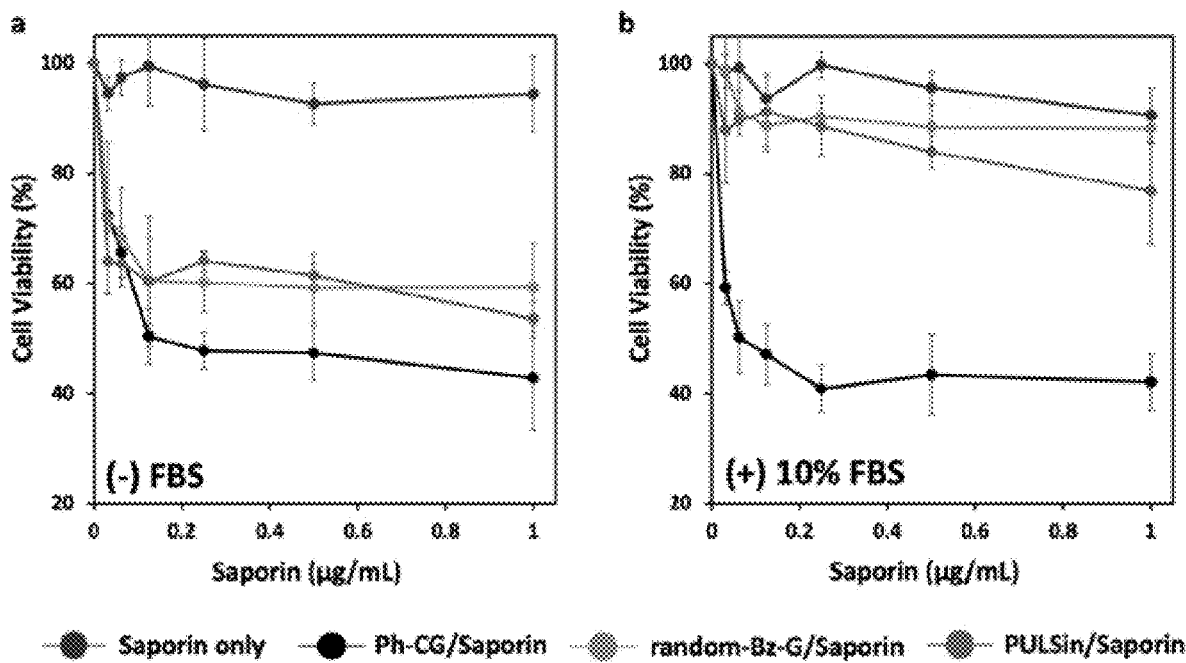
FIGS. 12A-12B show the viability of HeLa cells treated with Saporin complexes with Ph-CG, random-Bz-G, and PULSin, respectively, at various protein concentrations in a serum-free (12A) and a serum-containing medium (12B). The concentration of polymer was kept constant at 10 Free proteins were used as controls. Data represents the mean of 3 independent experiments+/−standard deviation.

Saporin is a ribosome inactivating protein that irreversibly blocks the synthesis of proteins in cells. RNase A is capable of degrading RNA chains and thus exhibiting toxic effects. While both cell membrane impermeable enzymes show no toxicity on HeLa cells, an exponential cell viability inhibition was observed when Saporin (32.8 kDa) was delivered by Ph-CG at less than 0.03 mg (FIGS. 12A-12B). It is noteworthy that this functional enzyme delivery was conducted in a serum containing medium and the efficiency is very similar regardless of the serum. The positive controls exhibit poor enzyme activities in the presence of serum, similarly to most of the reported systems.

Figures 13A, 13B:
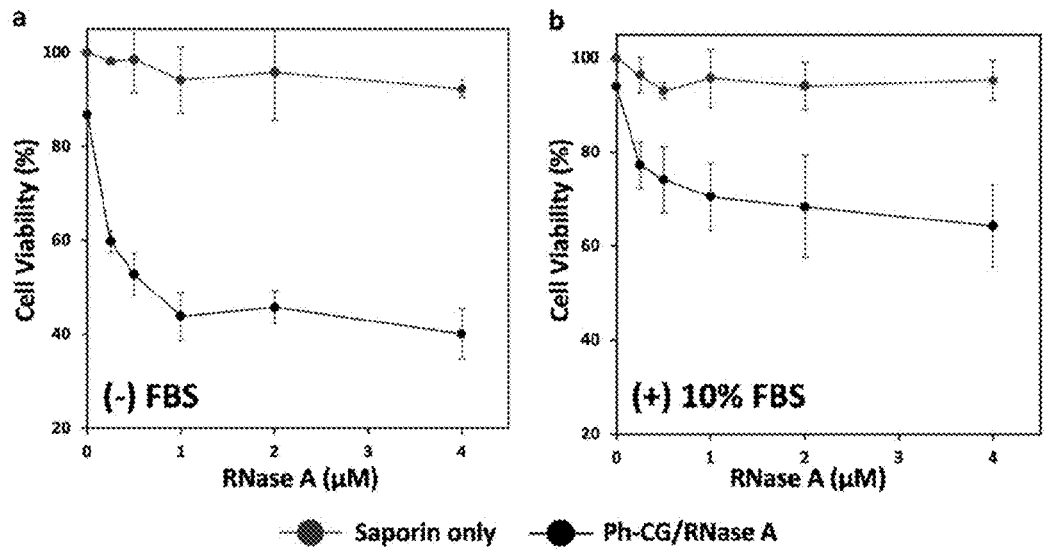
FIGS. 13A-13B show the viability of HeLa cells treated with RNase only and Ph-CG/RNase A complexes at various RNase concentrations in a serum-free (13A) and a serum-containing medium (13B). The concentration of polymer was kept constant at 10 μM. Data represents the mean of 3 independent experiments+/−standard deviation.
Figures 14A, 14B:
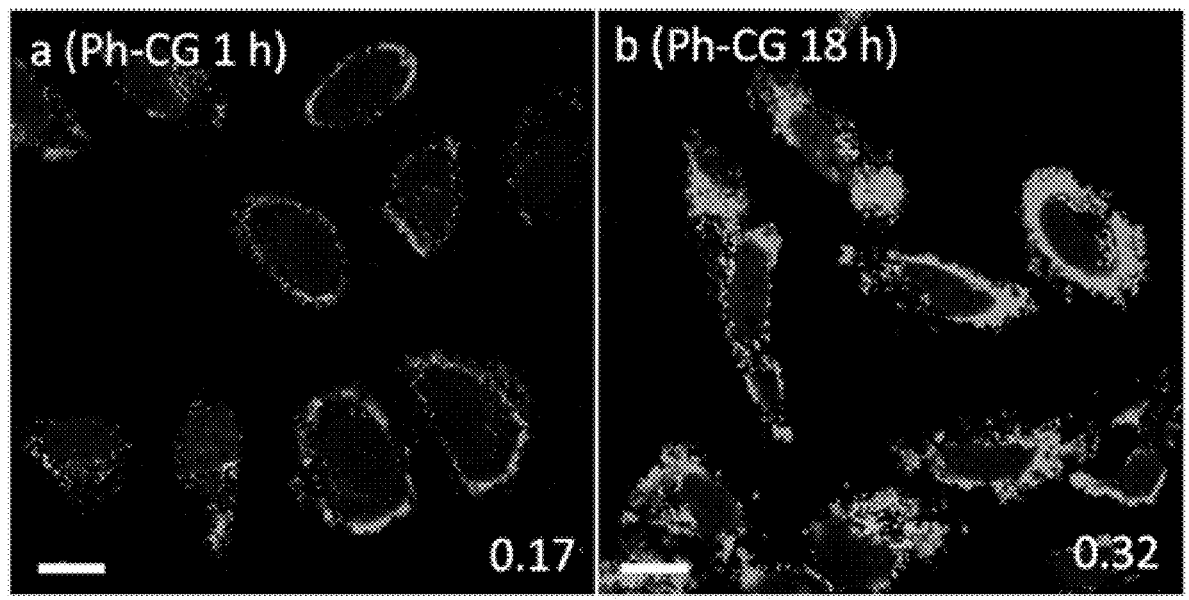
FIGS. 14A-14D show confocal images of HeLa cells treated with FITC-BSA/Ph-CG (a: 1 h and b: 18 h) and random-Bz-G (c: 1 h and d: 18 h) complexes. Blue: nucleus, green: FITC-BSA, red: Lysotracker. PCC scores were indicated at the lower right conner. Scale bar: 20 μm.
Figures 14C, 14D:
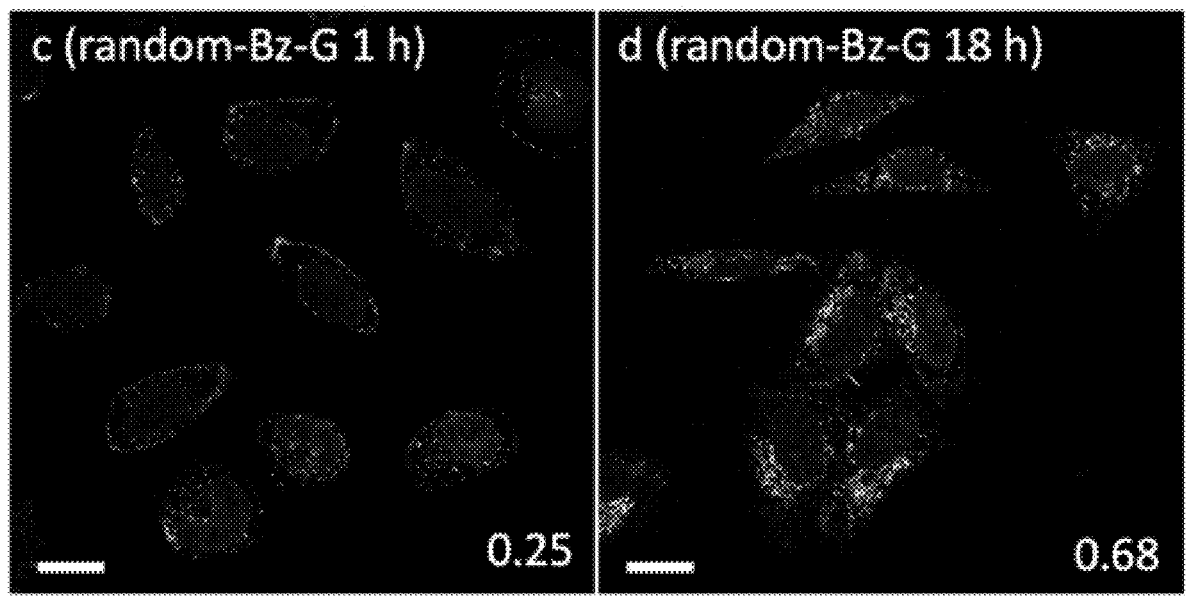
Figure 15A:
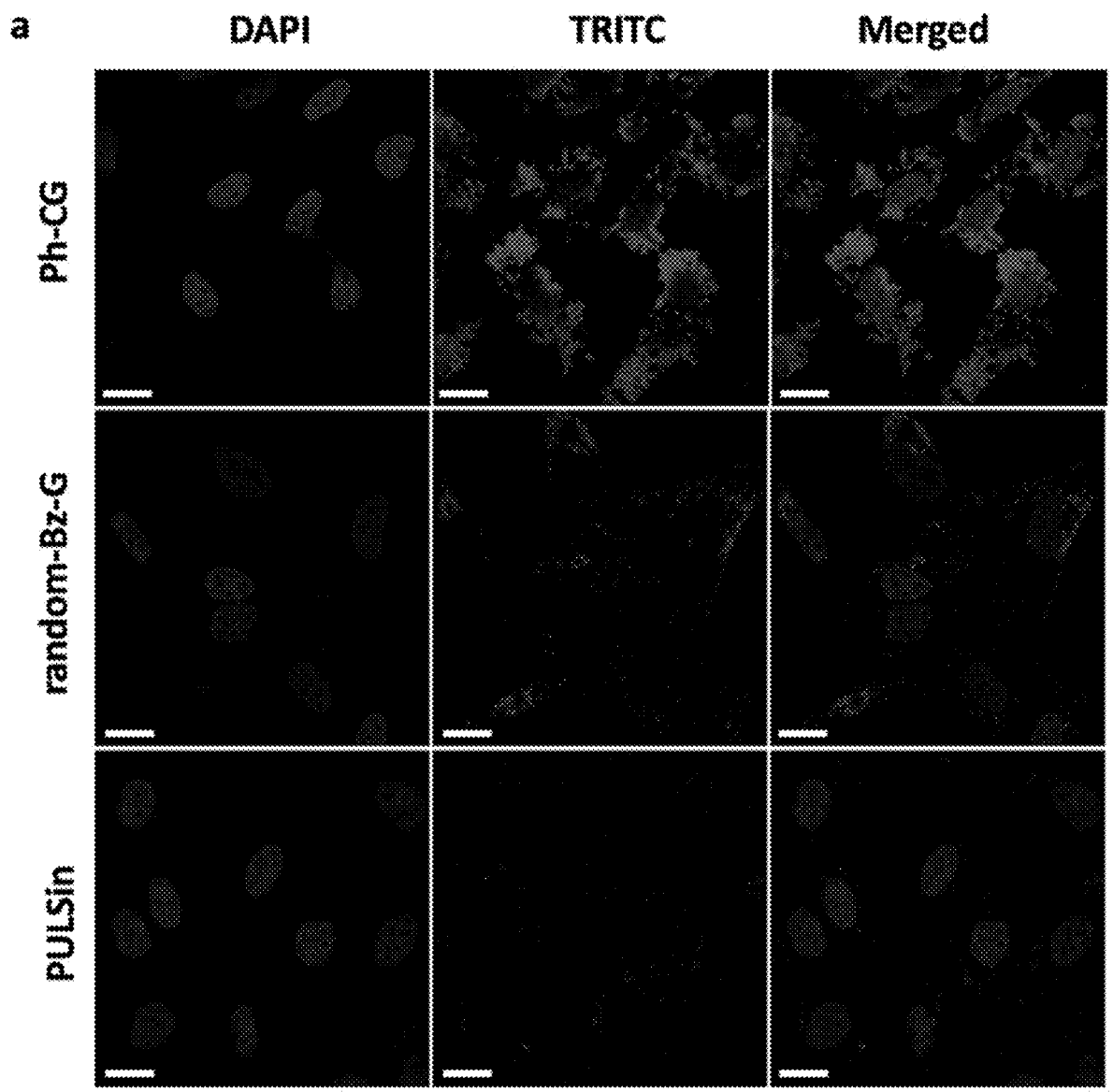
FIGS. 15A-15C show confocal microscope images of HeLa cells incubated with PN and PULSin complexes of R-PE (15A), FITC-BSA (15B), and EGFP (15C). Concentrations of PN, R-PE, FITC-BSA and EGFP were 10 μM, 15 nM, 100 nM and 100 nM, respectively.
Figure 15B:
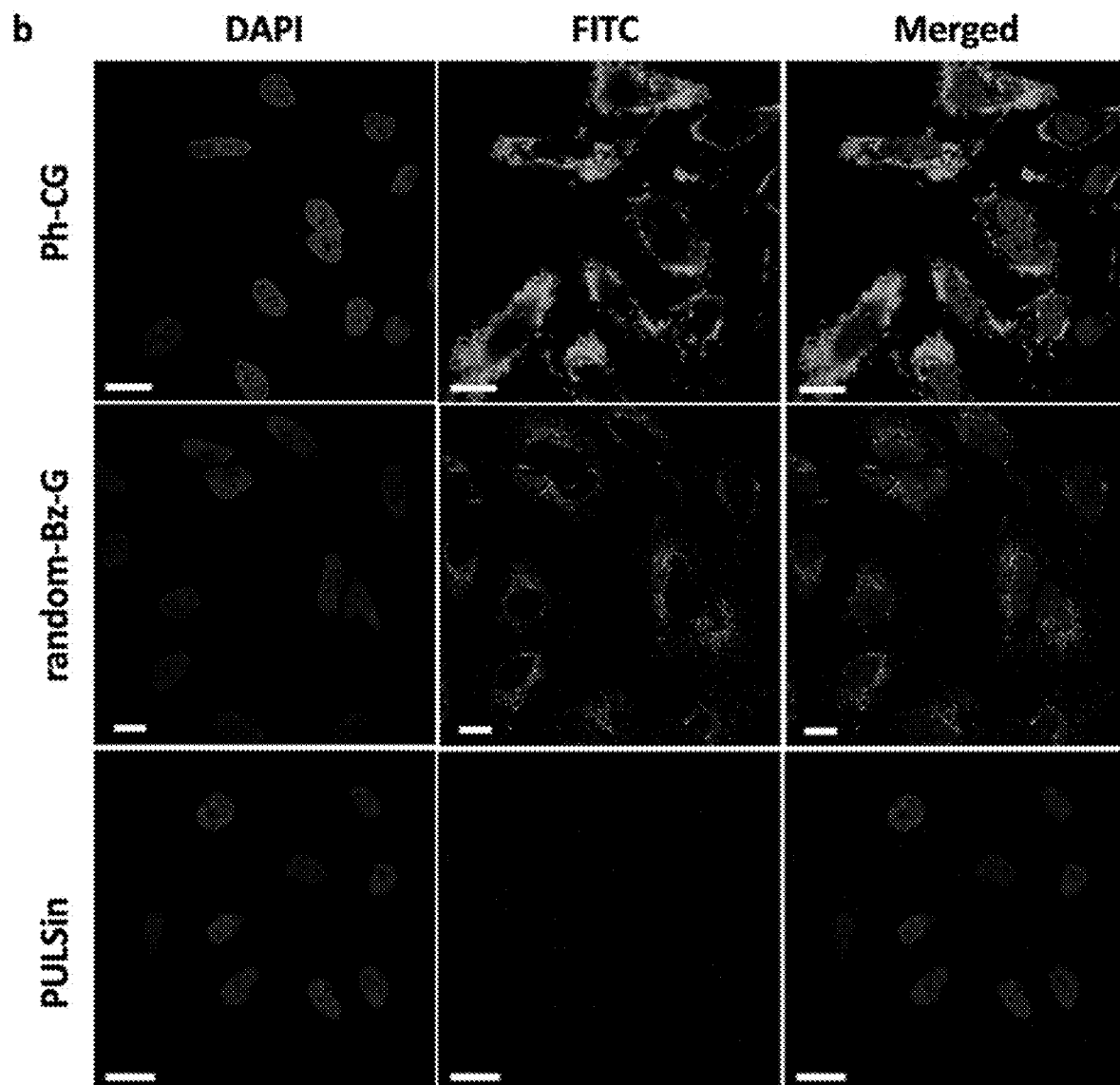
Figure 15C:
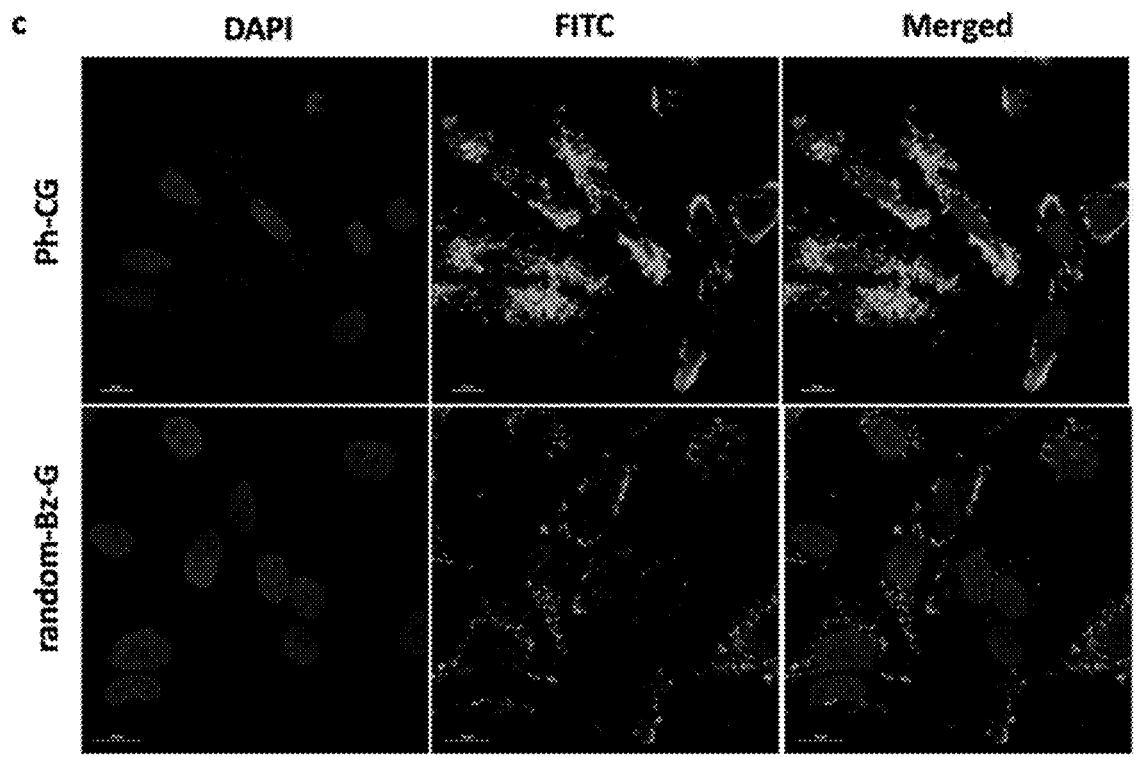

Delivered RNase by Ph-CG also shows concentration-dependent exponential cell viability decrease (FIGS. 13A-13B). However, RNase delivery was more efficient in a serum free medium, indicating that Ph-CG works better with larger proteins than RNase. Nevertheless, this viability inhibition result indicates that internalized proteins possibly escape from endosomes and/or use different pathways (e.g., via leaky macropinosomes in micropinocytosis) to reach the cytosolic targets.

Example 5—Ph-CG for FITC-BSA Delivery

Confocal microscopic images of HeLa cells treated with Ph-CG/fluorescein isothiocyanate (FITC) labeled-BSA show a diffused but intense cytosolic staining pattern that is quite different from the characteristic puncta (FIGS. 14A-14D and FIGS. 15A-15C for other FPs).

To determine whether FITC-BSA delivered by Ph-CG and random-Bz-G, respectively, are localized in acidic endosome/lysosome, cells were counter stained with Lysotracker Red, and quantitatively analyzed the levels of overlap between green and red colors using the Pearson's correlation coefficient (PCC) method. Low PCC scores of 0.17 and 0.25 were calculated from cells treated for 1 h with Ph-CG and random-Bz-G, respectively, indicating FITC-BSAs are not in acidic organelles.

When the treatment time increased to 18 h, the PCC score from the control random-Bz-G treated cells increased substantially (i.e., 0.68), indicating high FITC-BSAs localization in the endosome/lysosome. Meanwhile, the low PCC score (0.32) of 18 h Ph-CG/FITC-BSA treated cells indicates that the location of FITC-BSA is not in acidic organelles.

Example 6—Cellular Delivery Using Carbamoylated Derivatives of Guanidine

Figure 16A:
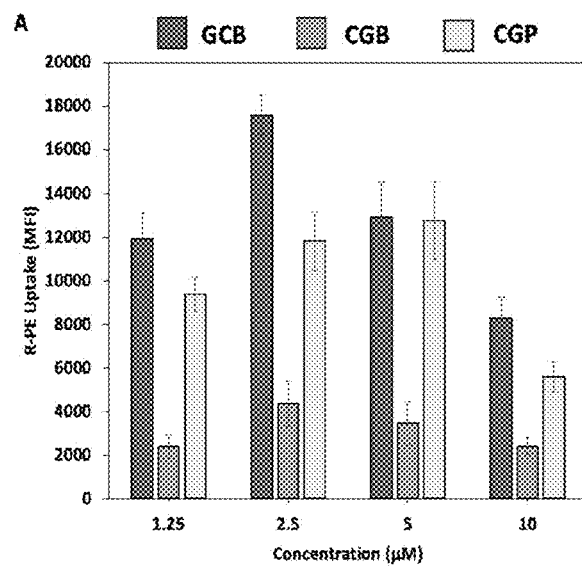
FIGS. 16A-16B show mean fluorescence intensity (16A) and R-PE positive cells (16B) of HeLa cells treated with PN/R-PE complexes for 18 h. The concentration of R-PE was 2 nM, and polymers were screened from 1.25 to 10 μM. Data shown is the mean of three independent experiments±standard deviation.
Figure 16B:
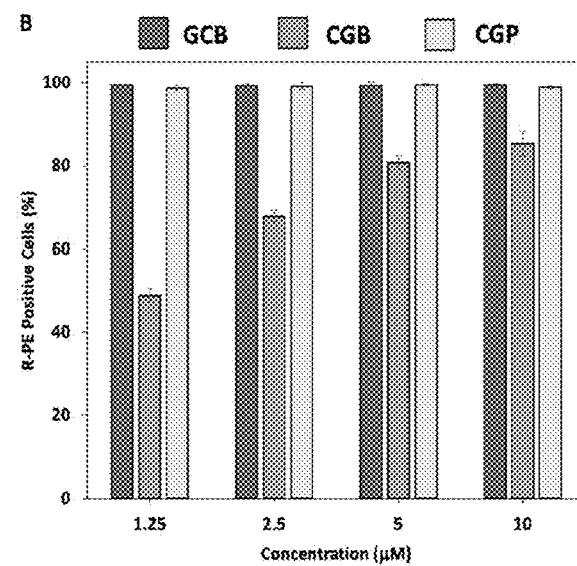
Figure 17:
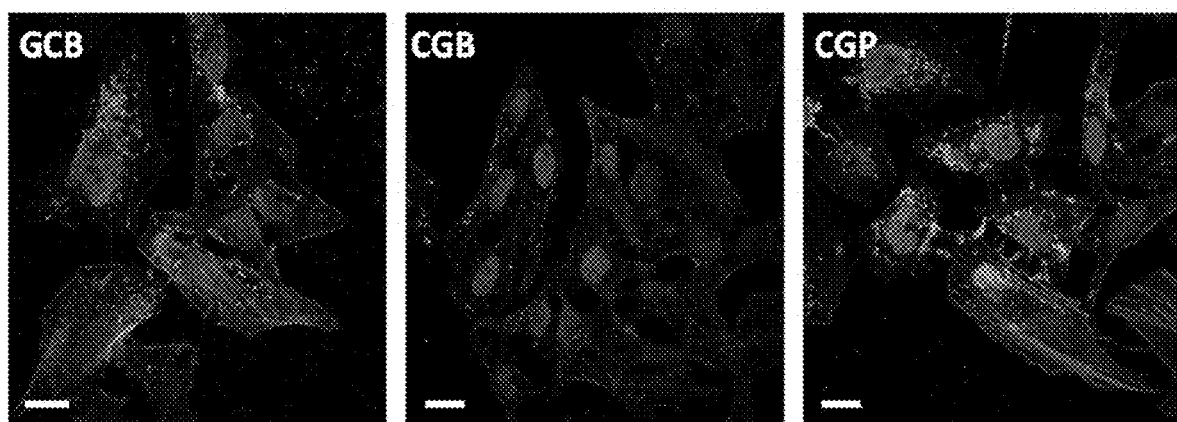
FIG. 17 shows confocal images of HeLa cells treated with PN/EGFP complexes for 18 h. The concentration of PNs and EGFP was 10 μM and 80 nM, respectively. Blue: nucleus, green: EGFP, red: ActinRed. Scale bar: 20 μm.

PNs such as carbamoylguanidinybenzene (CGB) and carbamoylguanidinypyrimidine (CGP) were synthesized for intracellular protein delivery. To investigate the delivery of R-PE, a large (240 kDa) fluorescent protein, into HeLa cells, polymers were mixed with R-PE and allowed to self-assemble into nanoparticles for 30 minutes prior to treatment to cells. HeLa cells were incubated in the presence of complexes overnight prior to thorough rinsing and flow cytometric analysis. As seen in FIG. 16A, GCB achieved 3-5 folds improved R-PE delivery compared to a constitutional isomer CGB, at all tested ratios. Additionally, GCB was able to transfect the entire cell population, achieving 100% R-PE positive cells at all concentrations, while CGB required higher concentrations of PN. As seen in FIG. 17, confocal imaging of HeLa cells treated with PN/EGFP complexes show a diffuse green signal distributed around the cytosol.

Example 7—Additional Derivatives

Thiourea and selenourea derivatives of GCB and CGB may also be synthesized using appropriated reagents. For example, compound 15 can be synthesized from compound 5 and carbon disulfide (Scheme 13). The thiourea GCB and CGB may be synthesized from, for example, compound 15 and 1-phenylguanidine or 1-benzylguanidine. Selenourea monomer may be synthesized using 2,4-bis(phenyl)-1,3-diselenadiphosphetane-2,4-diselenide, [PhP(Se)(μ-Se)]$_2$ (Scheme 14).

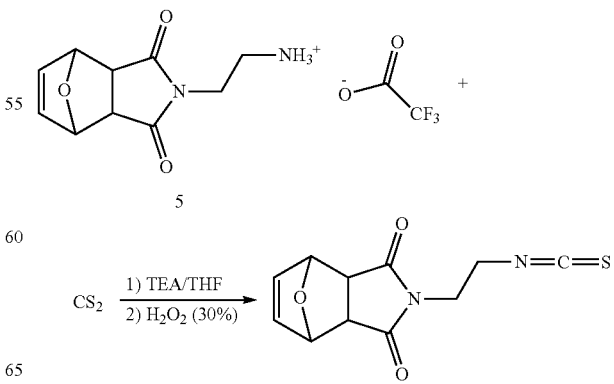

Scheme 14. Synthesis of selenourea monomer using 2,4-bis(phenyl)-1,3-diselenadiphosphetane-2,4-diselenide, [PhP(Se)(μ-Se)]₂.

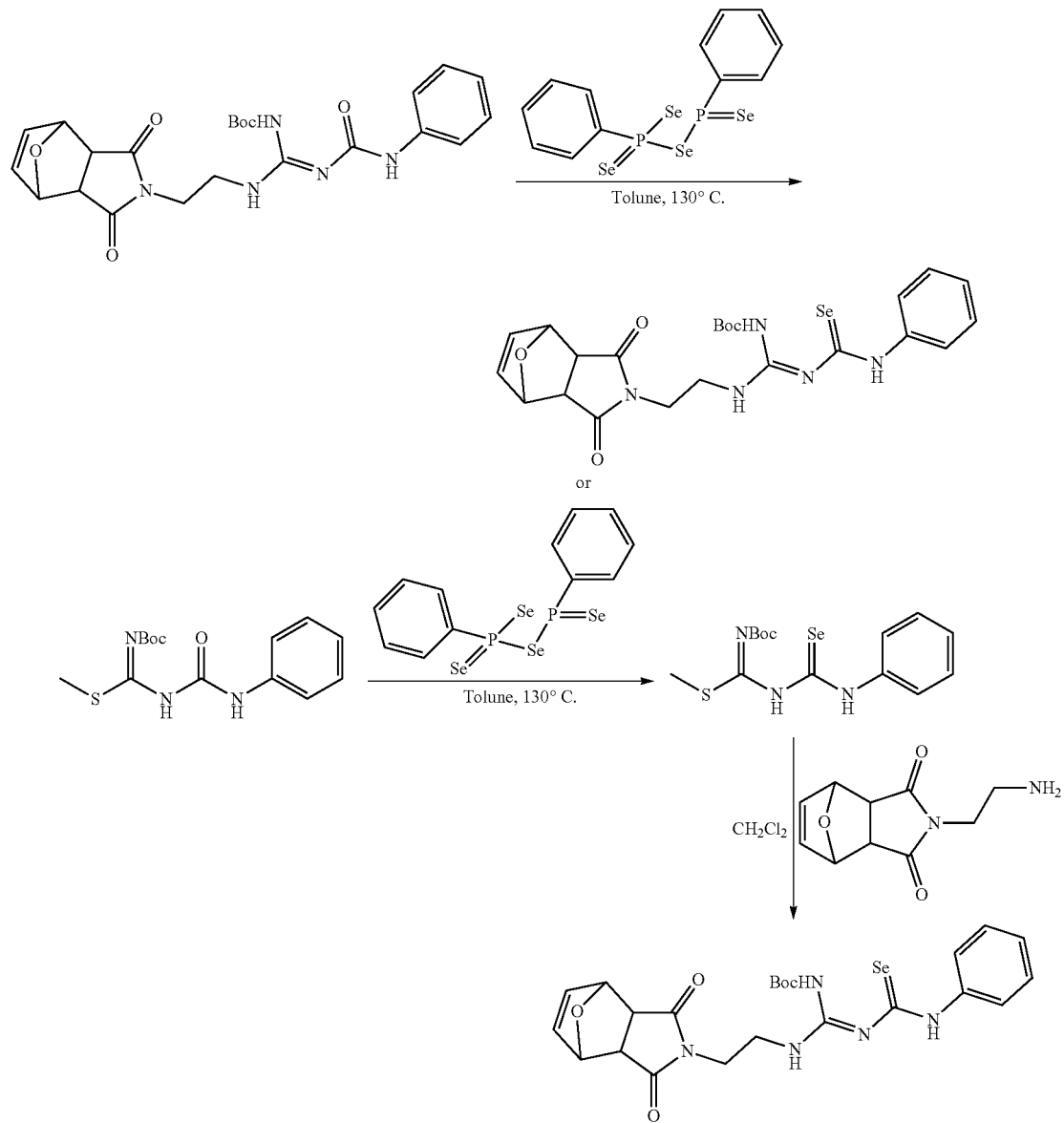

All patents and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A polymeric system comprising

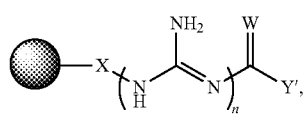

-continued

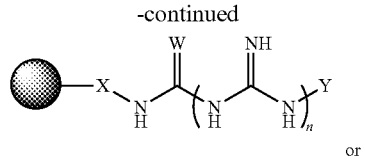

or

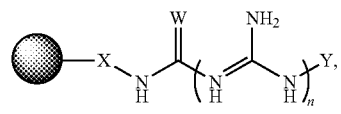

wherein

represents a backbone of a polymer, polysaccharide, protein, peptide, antibody, nucleic acid, metal organic framework or a nanoparticle; n≥1; W is S, O or Se; X is a linker, the linker being a C1-C20 alkylene, alkoxylene or heteroalkylene; Y and Y' are each independently selected from hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, hydroxyl, haloalkyl, amino, acyl, alkylamino, arylamino and hydroxylalkyl.

2. The polymeric system according to claim 1, the polymeric system comprising

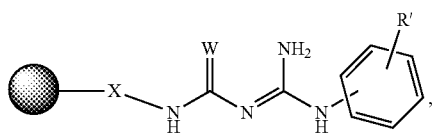

wherein R' is selected from hydrogen, halogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, amino, haloalkyl, hydroxyl, acyl, alkylamino, arylamino and hydroxylalkyl.

3. A composition comprising the polymeric system according to claim 1, a therapeutic agent and a pharmaceutically acceptable carrier.

4. The polymeric system of claim 1, wherein

represents the backbone of a polymer.

5. The polymeric system of claim 4, the polymer being amine functionalized polymethacrylates or polyacrylates, branched or linear polyehtyleneimines, polyamidoamine, amine functionalized dendrimers, poly-L-lysine, chitosan, amine functionalized dextran, amine functionalized alginates, amine functionalized heparin, or amine functionalized oligo or polysaccharide.

6. The polymeric system of claim 5, the polymer being poly-L-lysine.

7. The polymeric system of claim 1, X being C1-C10 heteroalkylene.

8. The polymeric system of claim 7, X being —(CH$_2$CH$_2$O-)n-, wherein n=1-100.

9. The polymeric system of claim 1, Y and Y' each independently being selected from phenyl (Ph), benzyl (Bz), phenylpropyl (PhPr), phenylbutyl (PhBu), hexylamine (HA), benzylamine (BA), and aminoethoxyethanol (AEE).

10. The polymeric system of claim 1, Y and Y' each independently being selected from

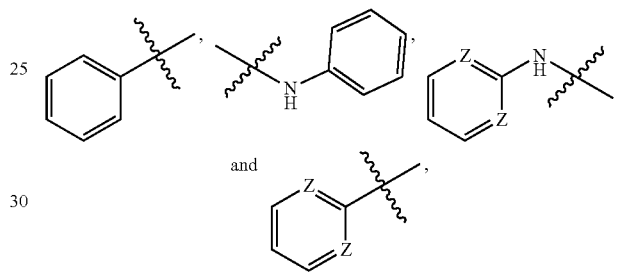

each Z being C or N.

11. The polymeric system of claim 1, comprising

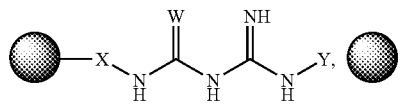

being poly-L-lysine; W is O; X is —(CH$_2$CH$_2$O—)n-, wherein n=2; and Y is Ph.

12. A composition comprising the polymeric system of claim 1.

* * * * *